(12) United States Patent
Matsumoto

(10) Patent No.: US 8,123,771 B2
(45) Date of Patent: Feb. 28, 2012

(54) LANCING UNIT, LANCING MEMBER REMOVAL TOOL AND LANCING APPARATUS

(75) Inventor: Daisuke Matsumoto, Kyoto (JP)

(73) Assignee: Arkray, Inc. (JP)

( * ) Notice: Subject to any disclaimer, the term of this patent is extended or adjusted under 35 U.S.C. 154(b) by 1249 days.

(21) Appl. No.: 10/523,176

(22) PCT Filed: Jul. 28, 2003

(86) PCT No.: PCT/JP03/09582
§ 371 (c)(1),
(2), (4) Date: Jan. 28, 2005

(87) PCT Pub. No.: WO2004/010871
PCT Pub. Date: Feb. 5, 2004

(65) Prior Publication Data
US 2005/0288698 A1    Dec. 29, 2005

(30) Foreign Application Priority Data

Jul. 29, 2002  (JP) .................................. 2002-220051

(51) Int. Cl.
*A61B 17/14*   (2006.01)
*A61B 5/00*   (2006.01)
(52) U.S. Cl. ........................................ 606/181; 600/583
(58) Field of Classification Search .................. 606/181, 606/183; 600/583; 206/364, 365
See application file for complete search history.

(56) References Cited

U.S. PATENT DOCUMENTS

| | | | | |
|---|---|---|---|---|
| 5,014,718 A | * | 5/1991 | Mitchen | .................... 606/181 |
| 5,207,699 A | | 5/1993 | Coe | |
| 5,324,303 A | | 6/1994 | Strong et al. | |
| 5,454,828 A | * | 10/1995 | Schraga | .................... 606/181 |
| 5,554,166 A | | 9/1996 | Lange et al. | |
| 5,879,311 A | * | 3/1999 | Duchon et al. | ............. 600/583 |

FOREIGN PATENT DOCUMENTS

| | | |
|---|---|---|
| DE | 43 20 463 | 12/1994 |
| EP | 0 589 186 | 3/1994 |
| JP | 6-23505 | 3/1994 |
| JP | 6-70915 | 3/1994 |
| JP | 6-38909 | 5/1994 |
| JP | 2000-166902 | 6/2000 |
| JP | 2000-175889 | 6/2000 |
| JP | 2000-225110 | 8/2000 |
| JP | 2001-133430 | 5/2001 |
| JP | 2003-515420 | 5/2003 |
| WO | WO 00/40150 | 7/2000 |
| WO | WO 01/41642 A1 | 6/2001 |

* cited by examiner

*Primary Examiner* — Julian Woo
(74) *Attorney, Agent, or Firm* — Studebaker & Brackett PC; Donald R. Studebaker

(57) ABSTRACT

A lancing unit (U) includes a support member (1) provided with engagement means (19A) which is inserted into a housing (4) of a lancing apparatus (A) for engagement with an engagement surface (24a) of a lancing member (2) when the lancing member (2) is mounted to a movable member (5) of the lancing apparatus. The removal of the lancing member (2) from the movable member (5) after the lancing member (2) is mounted to the movable member (5) can be easily and reliably performed by inserting the engagement means (19A) into the housing (4) and then pulling the engagement means out of the housing (4).

15 Claims, 25 Drawing Sheets

LANCING UNIT, LANCING MEMBER REMOVAL TOOL AND LANCING APPARATUS

TECHNICAL FIELD

The present invention relates to a lancing apparatus used to extract a sample such as blood, a lancing unit holding a disposable part as a unit and used as mounted to such a lancing apparatus, and a lancing member removal tool used for removing the lancing member mounted to a lancing apparatus.

BACKGROUND ART

Lancing apparatuses are often used for extracting blood of diabetics for measurement of the blood glucose levels. Generally, such a lancing apparatus includes a tubular housing having an open front end and a lancet holder arranged in the housing reciprocally movably. To use the lancing apparatus, a lancet of a disposable type is mounted to the lancet holder. Subsequently, with the front end of the housing held in contact with the skin of a human, the lancet and the lancet holder are advanced toward the front end of the housing so that the needle of the lancet lances the skin of the human. As a result, blood bleeds from the skin, whereby sampling of the blood can be performed.

FIGS. 26A, 26B, 27A and 27B show prior art lancets which are disclosed in JP-U 6-38909, for example.

The lancet 9A shown in FIG. 26A includes a threaded portion 94 and a needle 91. A cap 90A for covering the needle 91 is connected to the lancet 9A. When the threaded portion 94 is inserted into a housing 80 of a lancing apparatus 8 and rotated, the threaded portion is screwed to a threaded hole 82 provided at a front end of a lancet holder 81A of the lancing apparatus, whereby the lancet 9A is mounted to the lancet holder 81A. Thereafter, the cap 90A can be removed from the lancet 9A. After the lancing operation is performed, the cap 90A is reversed as shown in FIG. 26B and inserted into the housing 80. By fitting a hexagonal hole 92 formed in the lancet 90A to a hexagonal part of the lancet 9A and turning the cap, the screwed state of the lancet 9A and the lancet holder 81A is released, whereby the lancet 9A can be removed from the lancet holder 81A.

With such an arrangement, the user need not directly touch the needle 91 of the lancet 9A in mounting the lancet 9A to the lancing apparatus 8 and removing the lancet from the lancing apparatus 8. Therefore, it is possible to eliminate the possibility that the user's hand is hurt by the needle 91 or strained with blood adhering to the needle 91 by lancing.

The lancet 9B shown in FIG. 27A has a circumferential surface formed with projections 93. When the projections 93 are fitted into generally L-shaped grooves 83 formed in a lancet holder 81B of a lancing apparatus, the lancet 9B is held in the lancet holder 81B so as not to drop therefrom. After the lancet 9B is held in the lancet holder 81B in this way, the cap 90B can be removed from the lancet 9B, as shown in FIG. 27B. When the cap 90B is fitted to a portion having a cross-shaped section of the lancet 9B and rotated, the projections 93 can be removed from the grooves 83, whereby the lancet 9B can be removed from the lancet holder 81B. Also with such an arrangement, the user need not directly touch the needle 91, and the same advantages as those of the lancet shown in FIGS. 26A and 26B can be obtained.

However, the above prior art lancets have the following problems.

In the prior art lancet shown in FIGS. 26A and 26B, to remove the lancet 9A from the lancet holder 81A, the lancet 9A need be rotated by using the cap 90A. This rotation operation is troublesome for the user.

Although the cap 90A serves as a tool for rotating the lancet 9A, the cap does not have a function to positively and reliably hold the lancet 9A. Therefore, even when the screwed portion of the lancet 9A and the lancet holder 81A is loosened, the lancet 9A may not be taken out from the threaded hole 82. Further, in taking out the lancet 9A by fitting the lancet 9A to an end of the cap 90A, the lancet 9A may be removed from the cap 90A. Thus, the lancet 9A may not be properly taken out from the housing 80 just by using the cap 90A.

The above problems occur also in the lancet 9B shown in FIGS. 27A and 27B.

DISCLOSURE OF THE INVENTION

An object of the present invention is to provide a lancing unit, a lancing member removal tool and a lancing apparatus which are capable of solving or lessening the above-described problems.

According to a first aspect of the present invention, there is provided a lancing unit comprising a lancing member to be mounted, in use, to a lancing apparatus which includes a housing having a front end formed with an opening and a movable member provided in the housing reciprocally movably, and a support member for removably supporting the lancing member. The lancing member is capable of being fitted and mounted to the movable member so as to be capable of being pulled out of the movable member toward the front end side of the housing, and the lancing member includes an engagement surface which is oriented toward a rear side of the housing when the lancing member is mounted to the movable member. The support member includes engagement means which is inserted into the housing through the opening for engagement with the engagement surface when the lancing member is mounted to the movable member.

Preferably, the lancing member includes a needle, and a body supporting the needle.

Preferably, the body has an outer circumferential surface formed with a stepped portion comprising a recess or a projection, and the engagement surface is provided by the stepped portion.

Preferably, the engagement means includes at least one engagement projection extending in a first direction in which the needle of the lancing member extends and having a front end formed with a pawl projecting in a second direction crossing the first direction.

Preferably, in the lancing unit according to the present invention, the engagement means includes a plurality of engagement projections, and the engagement projections are engageable with the engagement surface in such a manner as to clip the lancing member when the lancing member is mounted to the movable member.

Preferably, the stepped portion of the body comprises a flange, and pawls of the engagement projections are spaced from each other by a distance which is smaller than the outer diameter or the width of the stepped portion. When the engagement projections are inserted into the housing in a state in which the lancing member is mounted to the movable member, each of the engagement projections resiliently deforms in the second direction due to contact with the stepped portion so that each of the pawls passes over the stepped portion.

Preferably, the support member includes a cap for covering the needle of the lancing member and removably supporting the lancing member.

Preferably, the boundary portion between the body and the cap has a structure which is more liable to receive stress than other portions of the body and the cap.

Preferably, the support member includes a tubular portion which is capable of being slid along and fitted to the front end of the housing, and the lancing member and the engagement means are arranged in the tubular portion. Herein, the "tubular potion" may not be circular but may be square or rectangular in cross section (which holds true for the following description).

Preferably, the lancing unit according to the present invention further comprises an analytical part and additional engagement means. The analytical part is removably supported by the support member so that the analytical part can be mounted at a predetermined position in the lancing apparatus in mounting the lancing member to the movable member. The analytical part includes an engagement surface which is oriented toward a rear side of the housing when the analytical part is mounted to the predetermined position. When the additional engagement means is inserted, through the opening, into the housing in a state in which the analytical part is separated from the support member and mounted to the predetermined position in the lancing apparatus, the additional engagement means engages the engagement surface of the analytical part.

Preferably, the additional engagement means includes an additional engagement projection extending in a first direction in which the needle of the lancing member extends and having a front end formed with a pawl projecting in a second direction crossing the first direction.

Preferably, the support member includes a tubular portion which is capable of being slid along and fitted to the front end of the housing. The lancing member, the analytical part, the engagement means and the additional engagement means are arranged in the tubular portion.

Preferably, the engagement means and the additional engagement means are so arranged as to enter the housing together when the tubular portion is slid along and fitted to the front end of the housing.

Preferably, the support member includes a partition wall partitioning the interior of the tubular potion into a first and a second chambers adjoining each other in an axial direction of the housing. The cap, the lancing member and the analytical parts are arranged in the first chamber, whereas the first and the second engagement means are arranged in the second chamber.

Preferably, the lancing unit according to the present invention further comprises a lid for hermetically closing the first chamber.

Preferably, the support member includes a chamber for accommodating the cap, the lancing member and the analytical part. The engagement means and the additional engagement means are also arranged in the chamber.

According to a second aspect of the present invention, there is provided a lancing member removal tool for removing a lancing member fitted and mounted to a movable member of a lancing apparatus, the apparatus including a housing which has a front end formed with an opening and in which the movable member is arranged reciprocally movably. The removal tool comprises engagement means for entering the housing through the opening for engagement with an engagement surface of the lancing member, and the engagement surface is oriented toward a rear side of the housing.

Preferably, the lancing member removal tool according to the present invention further comprises a support member including a tubular potion and supporting the engagement means. The engagement means engages the engagement surface of the lancing member when the tubular portion is slid along and fitted to the front end of the housing.

Preferably, the lancing member removal tool according to the present invention further comprises additional engagement means provided at the support member. When the tubular portion is slid along and fitted to the front end of the housing with an analytical part mounted to a predetermined position in the lancing apparatus, the additional engagement means enters the housing through the opening and engages an engagement surface of the analytical part, the engagement surface being oriented toward a rear side of the housing.

According to a third aspect of the present invention, there is provided a lancing apparatus comprising a housing having a front end formed with an opening, a movable member arranged in the housing reciprocally movably and having a front end to which the lancing member can be fitted, biasing means for biasing the movable member toward the front end of the housing, latching means for latching the movable member when the movable member is pushed deep into the housing more than a predetermined distance against a biasing force of the biasing means, and latch releasing means for releasing the movable member from the latched state provided by the latching means when a predetermined operation is performed. The apparatus further comprises a stopper capable of preventing the movable member from being pushed deep into the housing more than the predetermined distance.

Preferably, the stopper is capable of being positioned in a movement path of the movable member or a co-operating member moving together with the movable member and capable of contacting the movable member or the co-operating member to control retreating movement of the movable member.

Preferably, the housing is provided with a holding portion for removably holding an analytical part.

Other features and advantages of the present invention will become clearer from the description of the embodiments given below.

BRIEF DESCRIPTION OF THE DRAWINGS

FIG. 5A is a perspective view showing a sensor held by the sensor holder of FIG. 4, whereas

FIG. 20A is a sectional view showing another example of lancing unit according to the present invention, whereas

FIG. 22A is a sectional view showing another example of lancing unit according to the present invention, whereas

FIG. 23A is a sectional view showing an example of lancing member removal tool according to the present invention, whereas

BEST MODE FOR CARRYING OUT THE INVENTION

Preferred embodiments of the present invention will be described below in detail with reference to the accompanying drawings.

FIGS. 1-6 show an example of lancing unit according to the present invention.

Figure 1:
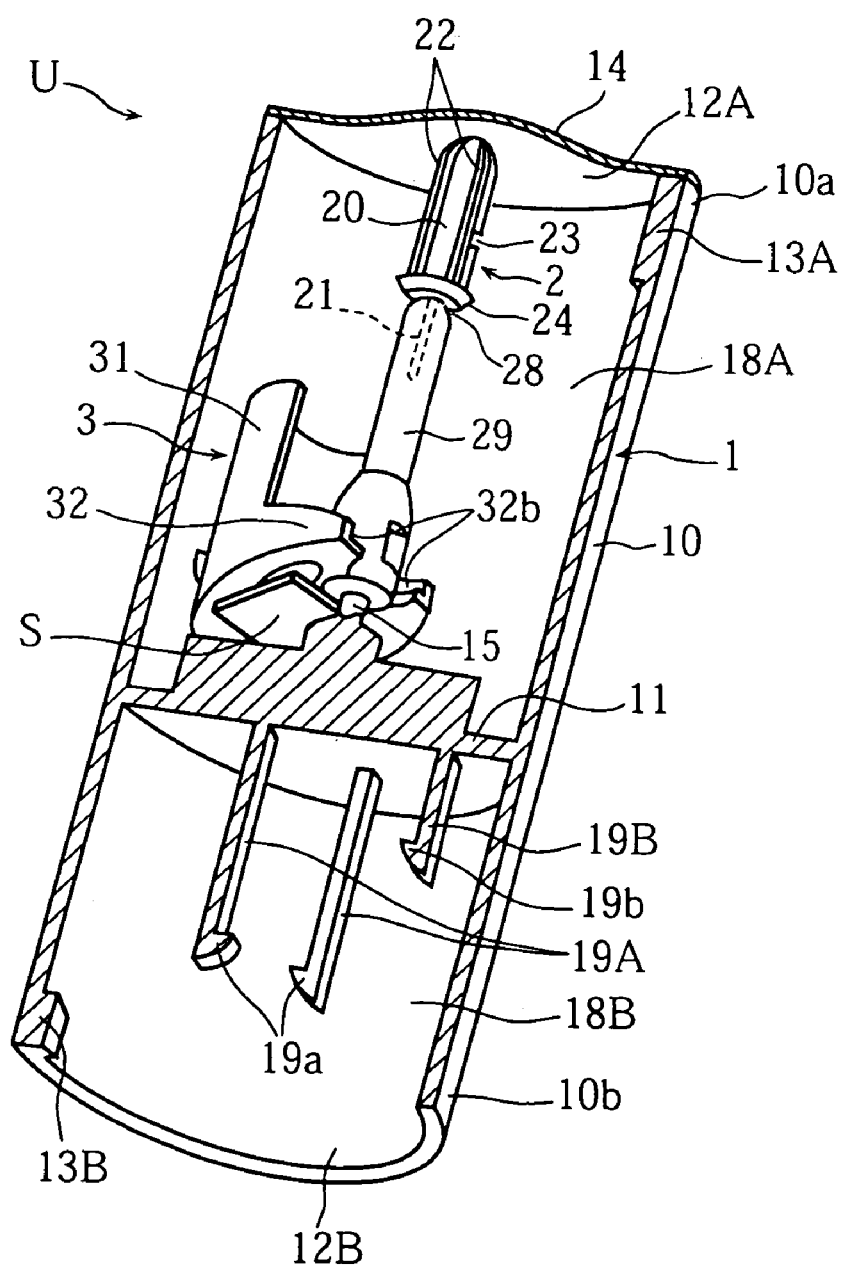
FIG. 1 is a perspective view, partially cut away, showing a lancing unit according to the present invention.
Figure 2:
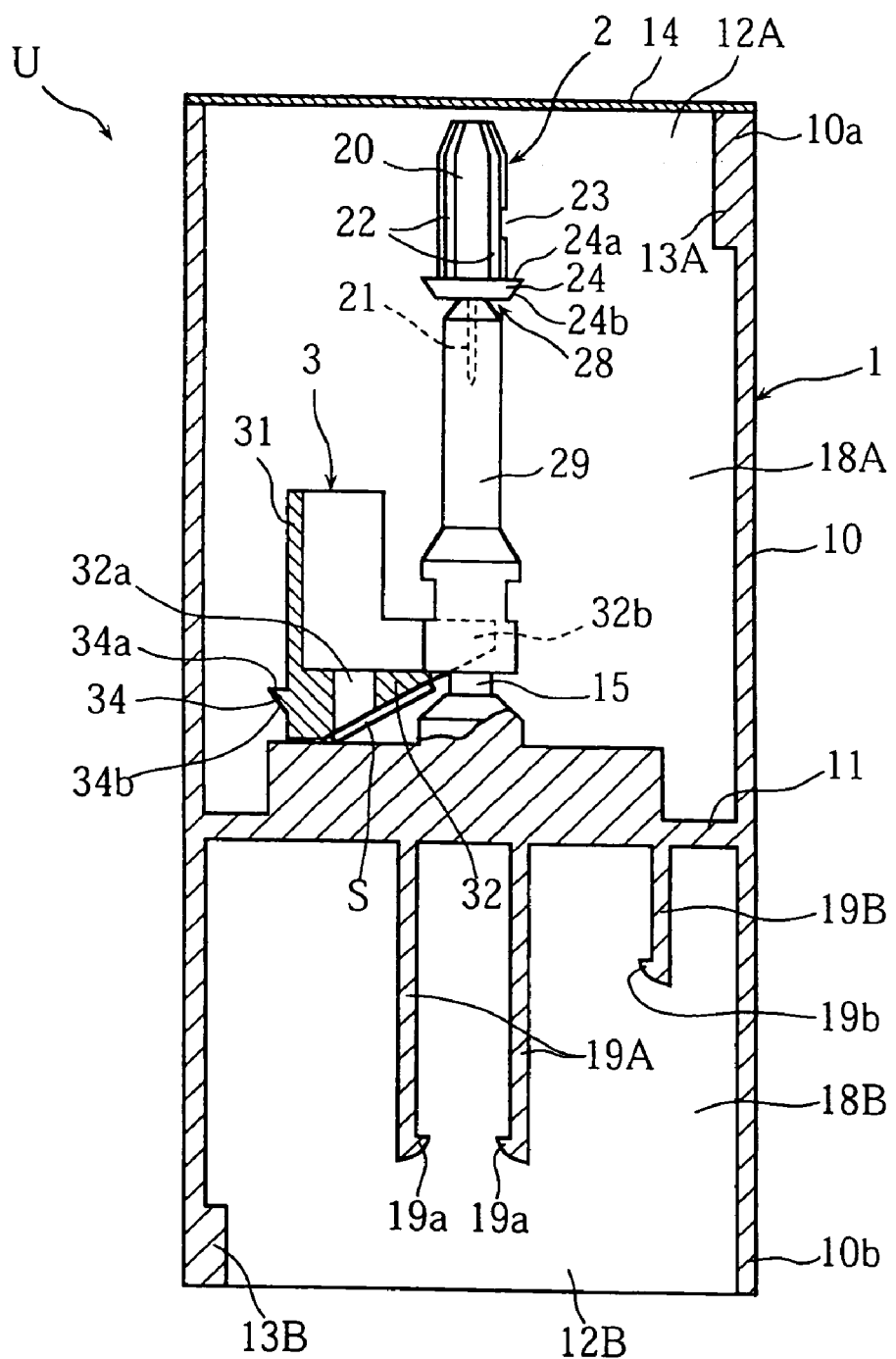
FIG. 2 is a side sectional view of FIG. 1.

As better shown in FIGS. 1 and 2, the lancing unit U of this embodiment includes a case 1, a lancet 2, a cap 29, a sensor holder 3, a pair of first engagement projections 19A and a second engagement projection 19B.

The case 1, which is made of e.g. synthetic resin, includes a generally cylindrical tubular portion 10 having a first end 10a and a second end 10b which are formed with openings 12A and 12B, respectively. The case further includes a partition wall 11 provided in the tubular portion 10. The partition wall 11 partitions the interior of the case 1 into a first and a second chambers 18A and 18B. The lancet 2, the cap 29 and the sensor holder 3 are arranged in the first chamber 18A. The paired first engagement projections 19A and the second engagement projection 19B are arranged in the second chamber 18B.

The first and the second ends 10a and 10b of the case 1 have inner circumferential surfaces respectively formed with projections 13A and 13B. As will be described later, the projections serve as a rotation stopper in fitting the case 1 around the front end of a housing 4 of a lancing apparatus A. The opening 12A is closed with a film 14 as a lid, whereby the first chamber 18A is hermetically closed. As the film 14, use may be made of one made of an aluminum foil or one provided by laminating a resin film to an aluminum foil.

Figure 3A:
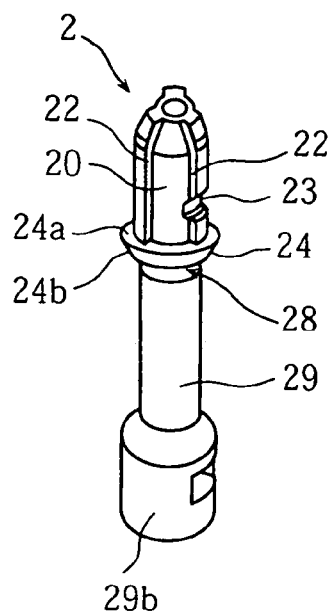
FIG. 3A is a perspective view showing a lancet with a cap, which is a structural part of the lancing unit of FIG. 1.
Figure 3B:
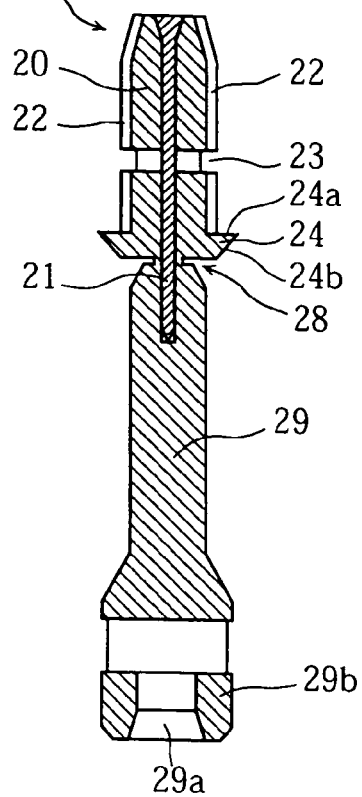
FIG. 3B is a sectional view thereof.

As better shown in FIGS. 3A and 3B, the lancet 2 includes a body 20 made of synthetic resin, and a needle 21 held by the body 20. The needle 21 includes a front end projecting from the body 20. The body 20 is so configured as to be properly mounted to a lancet holder 5 of the lancing apparatus A, which will be described later. The outer circumferential surface of the body 20 is formed with a recess 23, and a plurality of ribs 22 extending in the same direction as the needle 21. The outer circumferential surface of the body 20 is further formed, at the lower portion thereof, with an engagement step 24 in the form of a flange. The engagement step 24 is used in removing the lancet 2 from the lancet holder 5 and includes a generally horizontal surface 24a and a downward inclined surface 24b in a state in which the lancet 2 stands as shown in FIGS. 3A and 3B. The surface 24a is an example of engagement surface according to the present invention.

The cap 29 is formed integrally on the body 20 by resin-molding so as to cover the needle 21 and extends on the front end side (lower end side) of the body 20 in the same direction as the needle 21. The boundary portion 28 between the cap 29 and the body 20 is constricted for easy separation of these parts and is made smaller in diameter than other portions of the lancet 2 and the cap 29. As will be described later, the separation of the cap 29 from the lancet 2 is performed by twisting and breaking the boundary portion 28.

Figure 6:
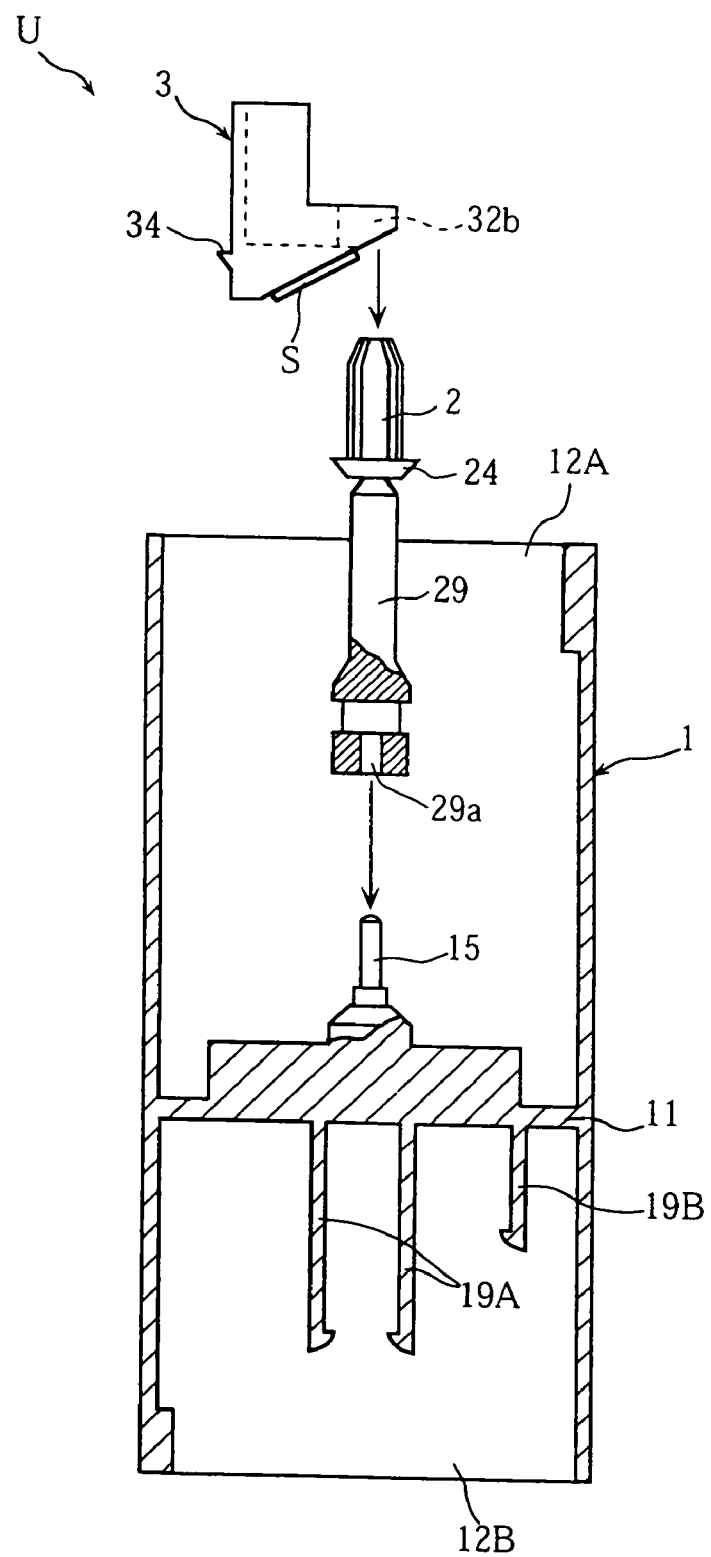
FIG. 6 is an exploded view, partially in section, of the lancing unit shown in FIG. 1.

The cap 29 has a lower end formed with a hole 29a. As shown in FIG. 6, the hole 29a can be fitted to a projection 15 projecting from the partition wall 11 of the case 1. By the fitting, the cap 29 is held in the case 1 in a standing posture. In the present invention, conversely to the above structure, the partition wall 11 of the case 1 may be formed with a recess, whereas the bottom of the cap 29 may be formed with a projection to be fitted in the recess. The cap 29 is bonded to the case 1 with an adhesive, for example. The cap 29 and the case 1 hold the lancet 2. Thus, the cap 29 and the case 1 are examples of a support member of the present invention. The cap 29 may be integrally formed on the case 1 by resin-molding. The needle 21 of the lancet 2 is subjected to sterilization by e.g. γ-ray irradiation before it is incorporated into the case 1. Preferably, the first chamber 18A further accommodates a desiccant (not shown) for keeping the quality of a sensor S, which will be described later.

Figure 4:
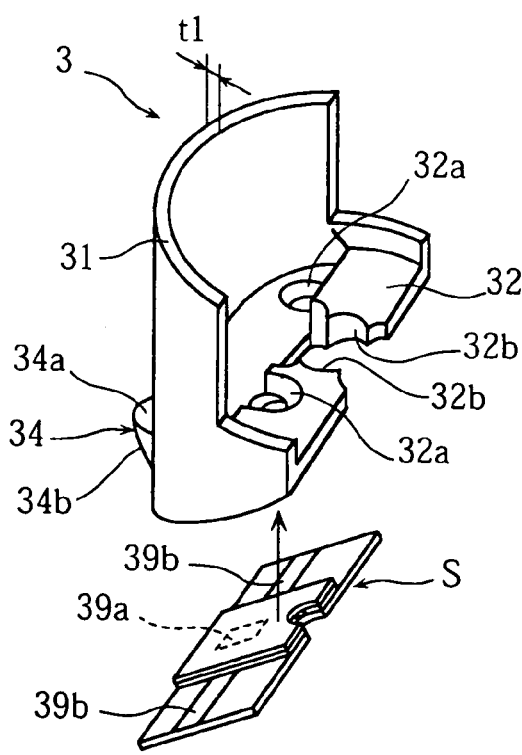
FIG. 4 is a perspective view showing a sensor holder which is a structural part of the lancing unit of FIG. 1.

The sensor holder 3 is an example of analytical part of the present invention. As better shown in FIG. 4, the sensor holder 3, which is made of synthetic resin, includes a main wall 32 and a side wall 31 connected to the main wall and having an arcuate cross section. The side wall 31 is formed with an engagement step 34 which is utilized for removing the sensor holder 3 when the sensor holder 3 is mounted to the lancing apparatus A, which will be described later. In the posture of the sensor holder 3 as shown in FIG. 4, the engagement step 34 has a generally horizontal upward surface 34a, and a downward, inclined surface 34b. The main wall 32 has a bottom surface which is inclined, for example, and to which the sensor S is attached.

Figure 5A:
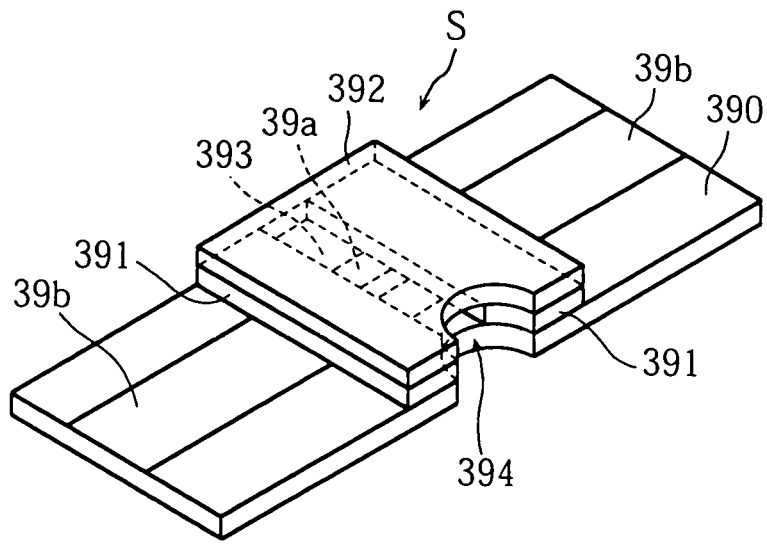
Figure 5B:
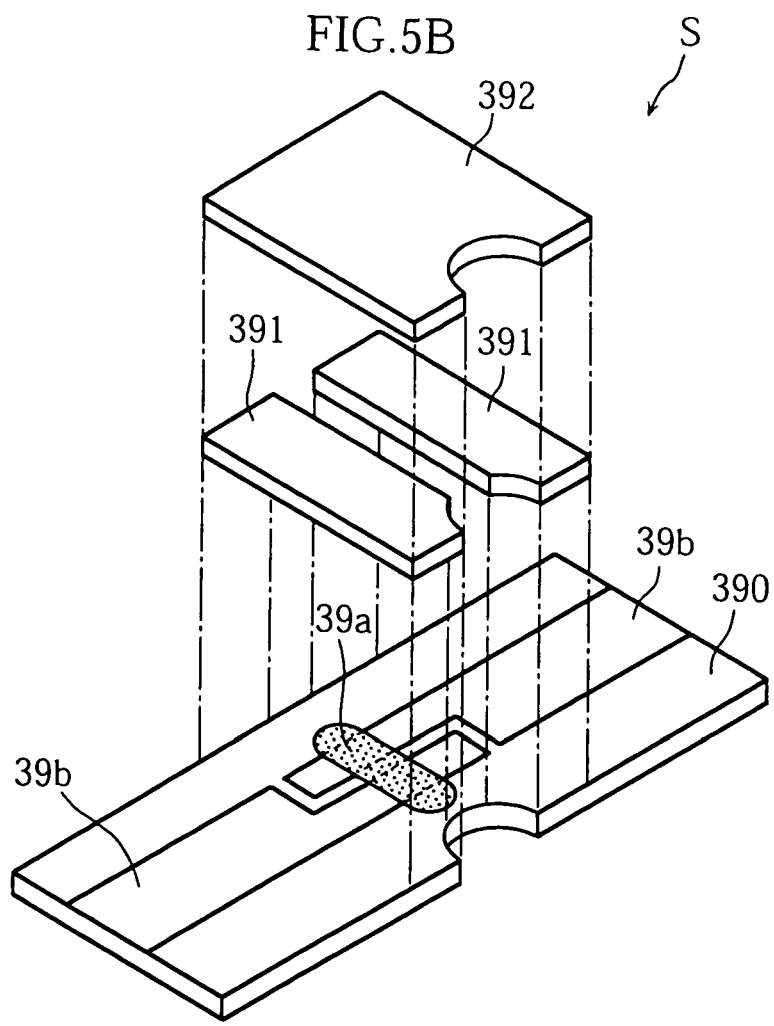
FIG. 5B is an exploded perspective view of the sensor.

The sensor S is in the form of a chip and has a structure as shown in FIGS. 5A and 5B, for example. The sensor S includes a substrate 390 on which are provided a reagent 39a containing enzyme which undergoes certain reaction (e.g. oxidation reaction) with glucose in blood, and a pair of electrodes 39b for electrically detecting the degree of the reaction. On the substrate 390 are also provided a pair of spacers 391 spaced from each other, and a cover 392 for covering the spacers 391, all of which serve to define a capillary 393. The substrate 390, each of the spacers 391 and the cover 392 are continuously formed with a recess 394 which serves as a blood introduction port. When blood is applied to the recess 394, the blood travels through the capillary 393 by capillary action and is guided to the reagent 39a.

As shown in FIG. 4, the main wall 32 of the sensor holder 3 is formed with a pair of through-holes 32a and a pair of holding walls 32b. The paired through-holes 32a are utilized for inserting a pair of measurement probes 62 of the lancing apparatus A1, which will be described later, so that the measurement probes 62 come into contact with the paired electrodes 39b of the sensor S. The paired holding walls 32b can be fitted around a lower portion 29b of the cap 29 so as to clip the lower portion from opposite sides. For example, the lower portion 29b of the cap 29 is columnar, whereas the paired holding walls 32b are curved into a generally arcuate shape corresponding to the outer circumferential surface of the lower portion. As shown in FIGS. 1 and 2, by fitting the paired holding walls 32b around the lower portion of the cap 29, the sensor holder 3 is attached to the case 1 via the cap 29. However, the sensor holder 3 is slidable upward for removal from the cap 29.

The paired engagement projections 19A and the second engagement projection 19B are formed integrally on the case 1 by resin-molding to be connected to the partition wall 11 and extends in the axial direction of the tubular portion 10. The projections are flexibly deformable, with elastic restoring force, in the direction crossing the axial direction of the tubular portion 10. The projections have front ends formed with pawls 19a, 19b projecting in the direction crossing the above-noted axial direction.

Figure 18:
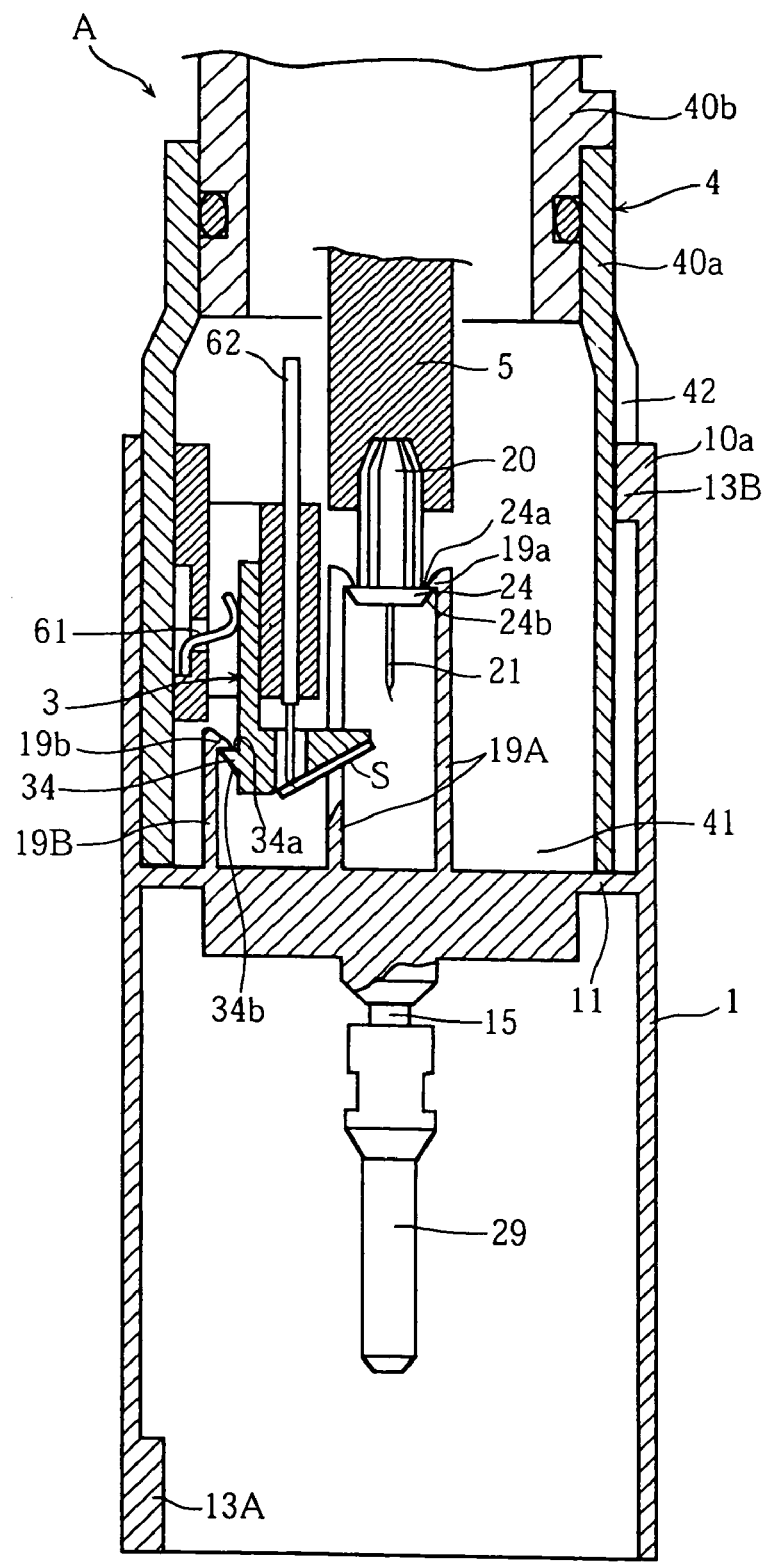
FIG. 18 is a sectional view of a principal portion showing the operation of removing the lancet and the sensor holder from the lancing apparatus.

As will be described later with reference to FIG. 18, the position and size of the first engagement projections 19A are so designed that the pawls 19a engage the surface 24a of the engagement step 24 of the lancet 2 held in the lancing apparatus A when the case 1 is fitted to a predetermined position of the lancing apparatus A. The distance between the pawls 19a of the paired first engagement projections 19A is slightly smaller than the outer diameter of the engagement step 24 of the lancet 2. The position and size of the second engagement projection 19B are so designed that the pawl 19b engages the surface 34a of the engagement step 34 of the sensor holder 3 held in the lancing apparatus A when the case 1 is fitted to a predetermined position of the lancing apparatus A.

Figure 7:
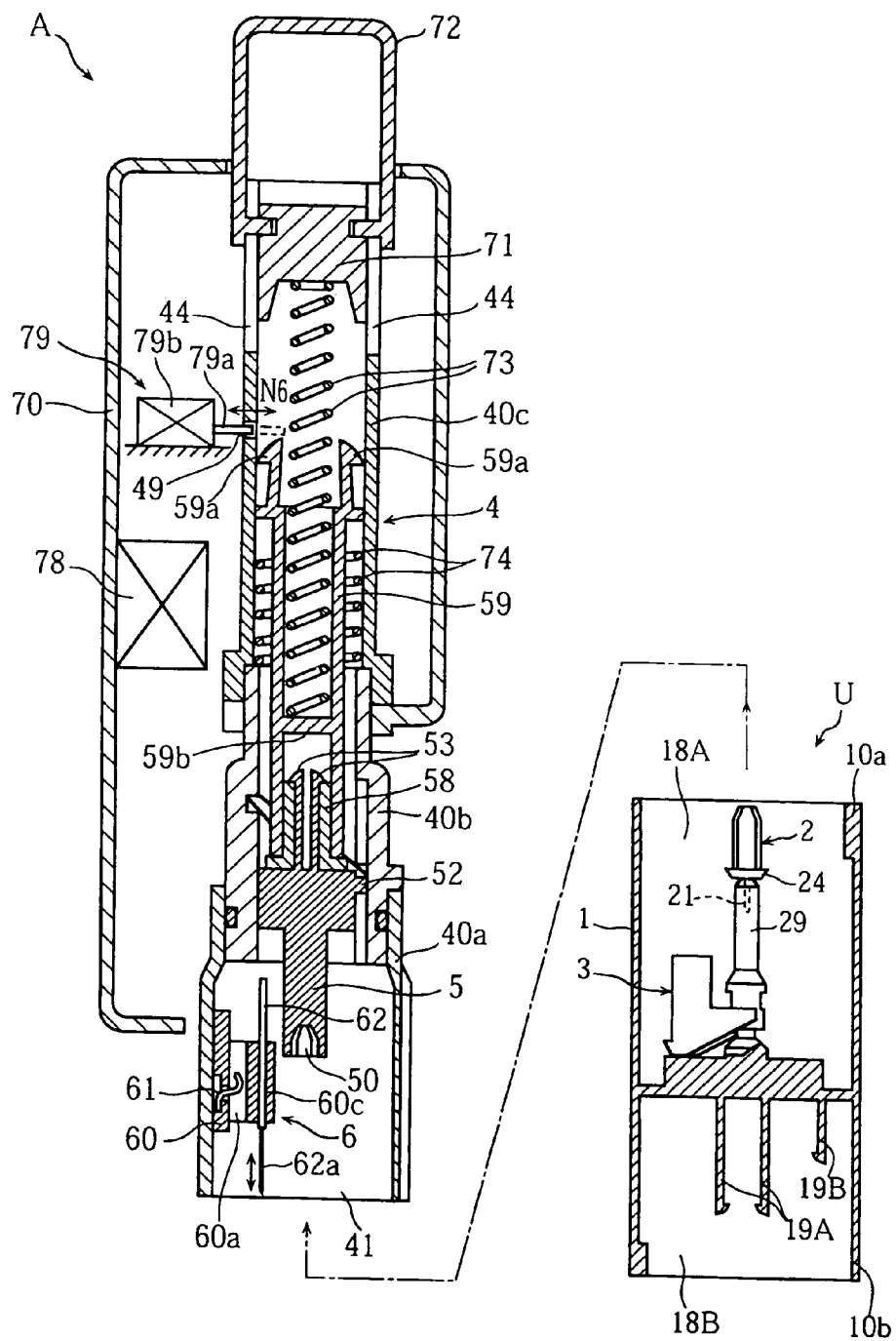
FIG. 7 is a sectional view showing an example of lancing apparatus according to the present invention.
Figure 8:
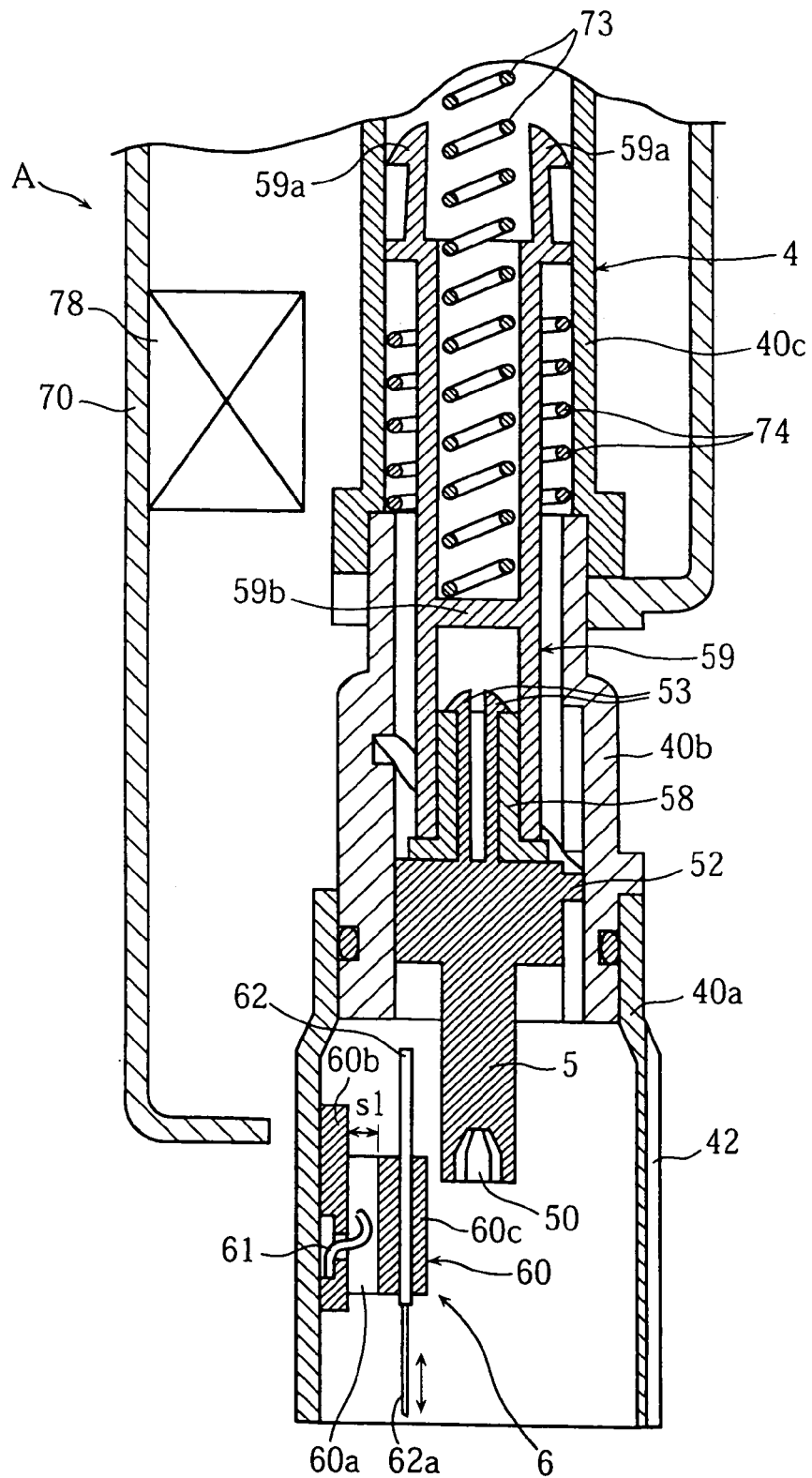
FIG. 8 is an enlarged sectional view of a principal portion of FIG. 7.

FIGS. 7 and 8 show an example of lancing apparatus according to the present invention.

As better shown in FIG. 7, the lancing apparatus A of this embodiment includes a housing 4, a lancet holder 5 arranged in the housing 4, a latch member 59 and a stopper mechanism 79.

The housing 4 is provided by connecting three sleeves 40a-40c in series and is fixed to an outer case 70. The sleeve 40a has a front end (lower end) which is to come into contact with the skin of a human body and which has an opening 41. The sleeve 40a is so designed that the case 1 of the lancing unit U can be slid on and fitted around the sleeve from either of the first end 10a and the second ends 10b. The outer surface of the sleeve 40a is formed with a groove 42 extending axially of the sleeve 40a. In fitting the case 1 around the sleeve 40a, the projections 13A and 13B of the case 1 are fitted in the groove, whereby the rotation of the case 1 is prevented. In the lancing apparatus A, in mounting the lancet 2 and the sensor holder 3 of the lancing unit U to the lancing apparatus A and in removing the lancet 2 and the sensor holder 3 from the apparatus, the case 1 is slid on and fitted to the sleeve 40a.

Figure 12:
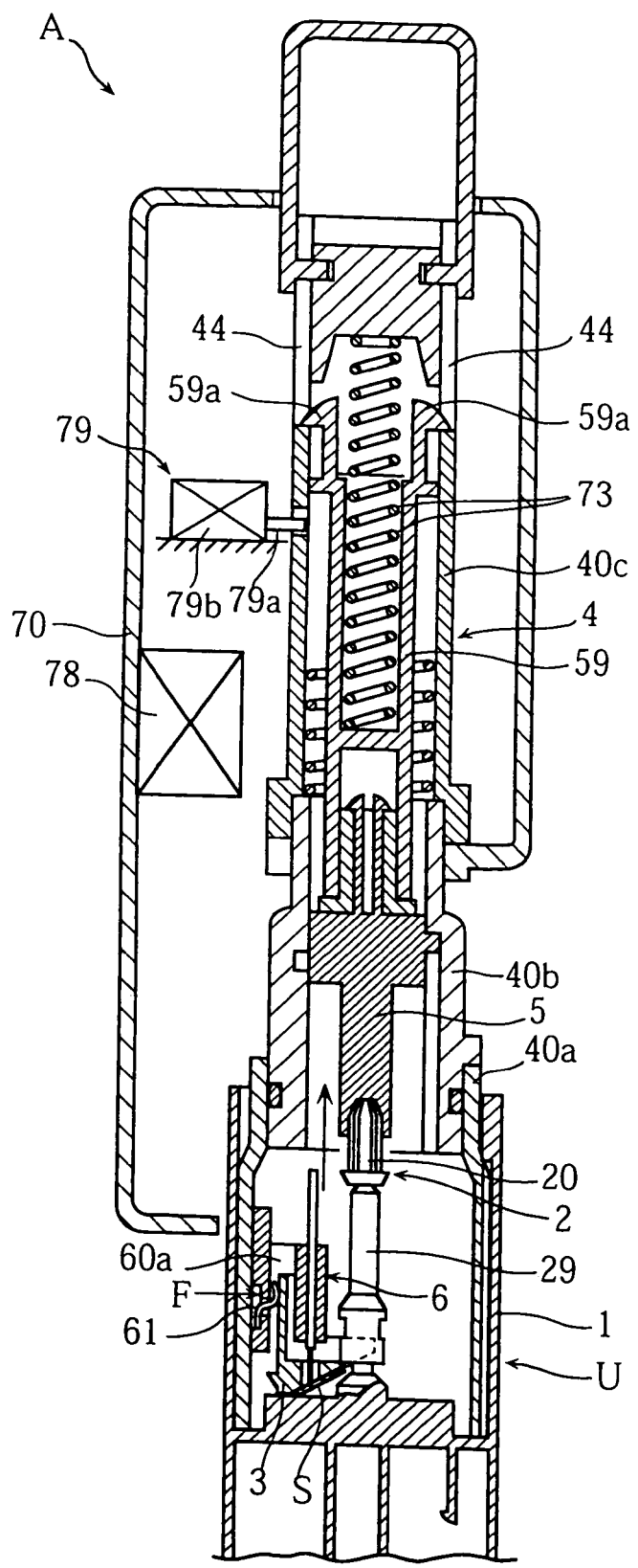
FIG. 12 is a sectional view of a principal portion in the process of mounting a lancet and a sensor holder to a lancing apparatus.
Figure 13:
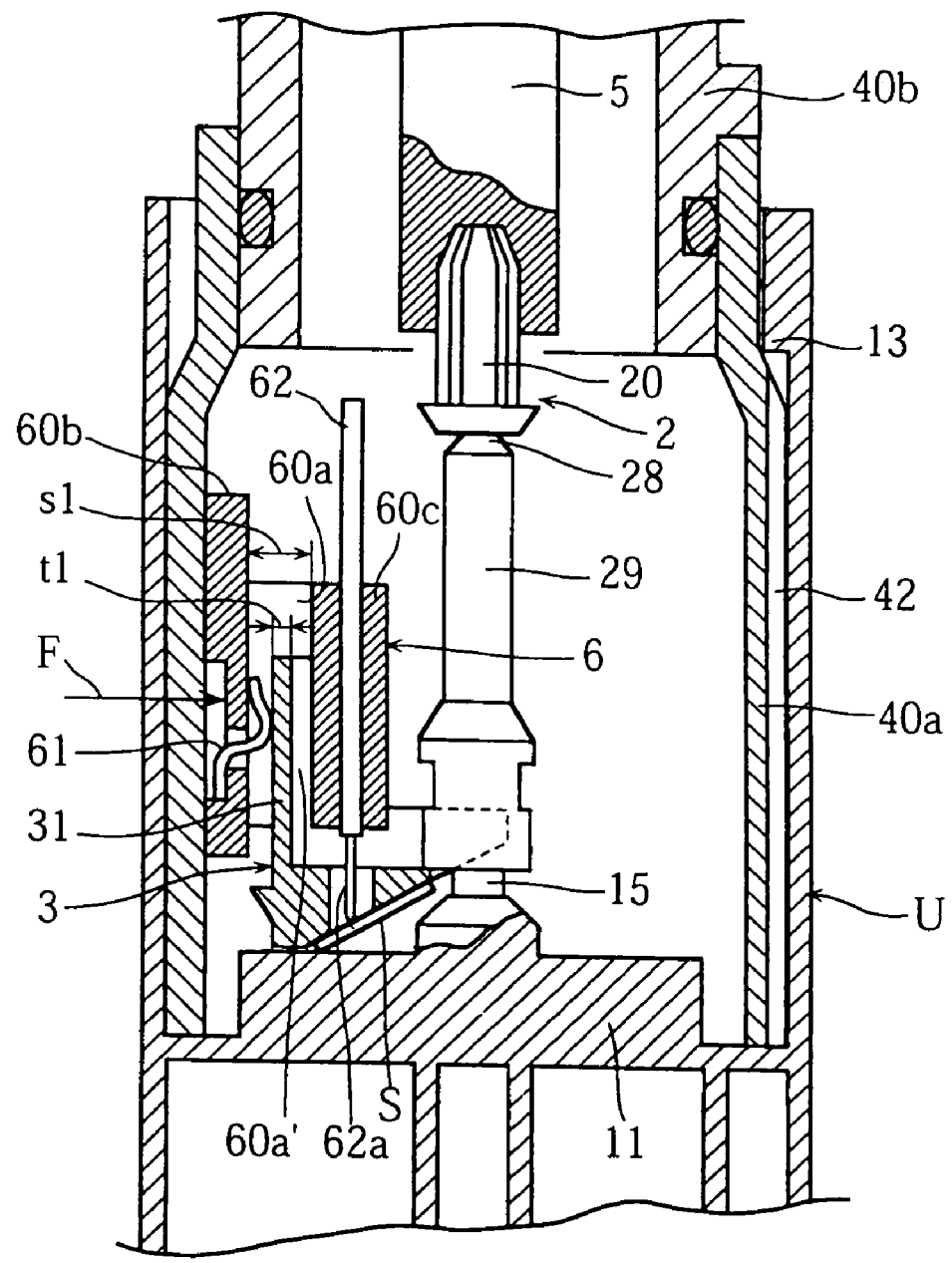
FIG. 13 is an enlarged sectional view showing a principal portion of FIG. 12.

As better shown in FIG. 8, in the sleeve 40a is provided a holding portion 6. The holding portion 6 serves to hold the sensor holder 3 of the lancing unit U and includes an attachment 60 made of synthetic resin and fixed to the inner surface of the sleeve 40a. The attachment 60 includes a first and a second walls 60b and 60c defining a space 60a. As shown in FIGS. 12 and 13, the space 60a is utilized for inserting the side wall 31 of the sensor holder 3 from below. In the holding portion 6 is provided a spring 61. When the side wall 31 of the sensor holder 3 enters the space 60a, the spring 61 exerts a resilient force F for pushing the side wall 31 toward the second wall 60c, i.e., toward the center of the sleeve 40a, whereby the sensor holder 3 is retained.

Figure 14:
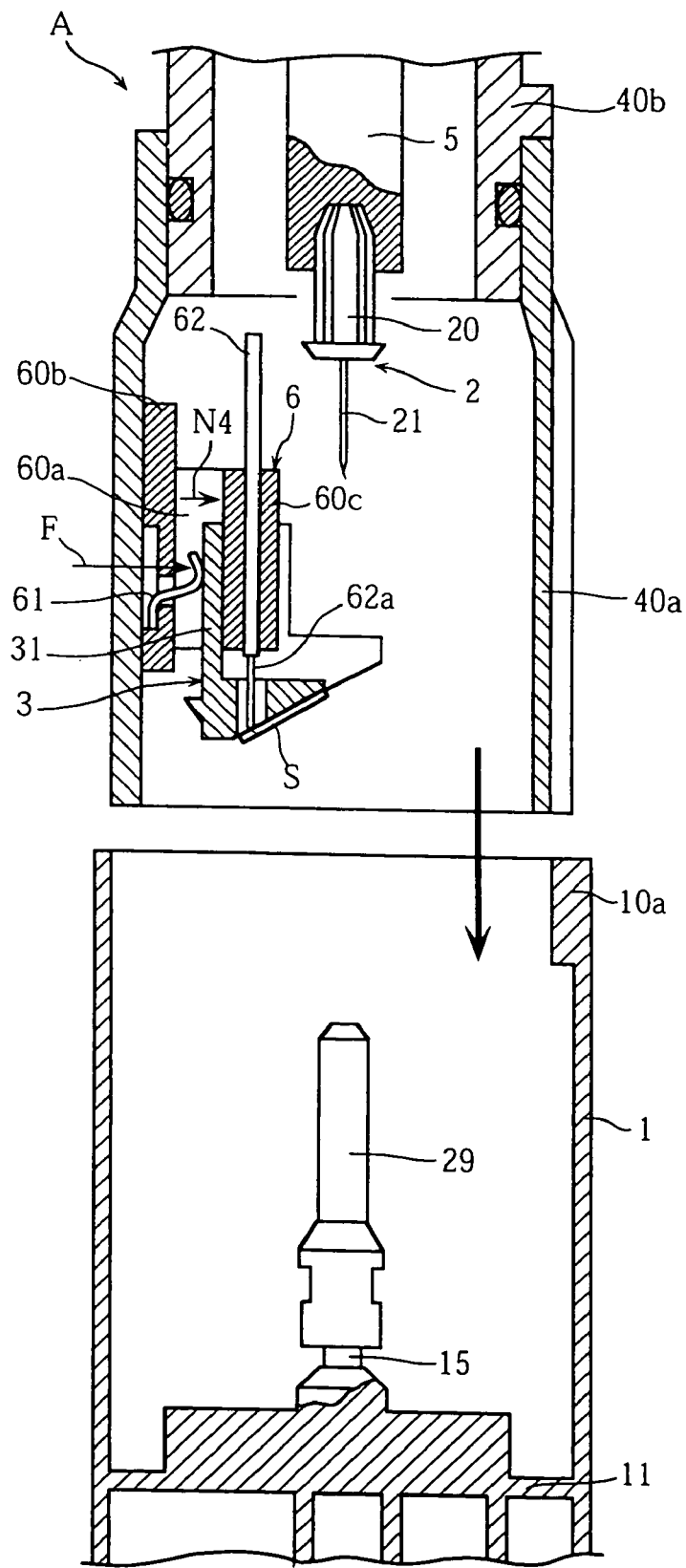
FIG. 14 is a sectional view showing a principal portion after the mounting of the lancet and the sensor holder to the lancing apparatus is completed.

As better shown in FIG. 13, the space 60a has a width s1 which is larger than the thickness t1 of the side wall 31 of the sensor holder 3. Therefore, when the side wall 31 of the sensor holder 3 attached to the case 1 is inserted into the space 60a, a gap 60a' is defined between the side wall 31 and the second wall 60c. On the other hand, when the sensor holder 3 and the cap 29 are separated from each other as shown in FIG. 14, the side wall 31 of the sensor holder 3 is pressed against a side surface of the second wall 60c by the resilient force F of the spring 61.

Referring to FIGS. 7 and 8, the paired measurement probes 62 are held in the second wall 60c. The paired measurement probes 62 for coming into contact with the paired electrodes 39b of the sensor S extend axially of the housing 4. Each of the measurement probes 62 has an expandable and contractible front end 62a which projects downward by a resilient force of an appropriate spring (not shown) when the sensor holder 3 is not mounted to the lancing apparatus A. As shown in FIGS. 12-14, when the sensor holder 3 is mounted to the holding portion 6, the front end 62a is pushed upward by the sensor S for contraction. The paired measurement probes 62 are electrically connected to a control circuit 78 provided in the outer case 70. The control circuit 78, which comprises e.g. a CPU and a memory attached thereto, performs computation of the glucose level in blood introduced to the reagent 39a based on the current detected via the paired measurement probes 62.

The lancet holder 5 is reciprocally movable while holding the lancet 2 and is an example of movable member of the present invention. The lancet holder 5 is fitted in the sleeve 40b rotatably and axially slidably. The lancet holder 5 has a lower end formed with a recess 50. By pushing the body 20 of the lancet 2 into the recess 50, the lancet 2 is fitted to and held by the lancet holder 5. To reliably hold the lancet 2, the lower end of the lancet holder 5 may be formed with one or a plurality of axially extending slits so that the lower end of the lancet holder 5 becomes radially expandable and contractible. With such an arrangement, when the body 20 is fitted into the recess 50, the lower end of the lancet holder 5 holds the body 20 tightly with an appropriate resilient force. Alternatively, the lancet holder 5 may be formed with a portion for engaging the recess 23 of the body 20 so that easy dropping of the body 20 from the recess 50 is prevented by the engagement.

Figure 9:
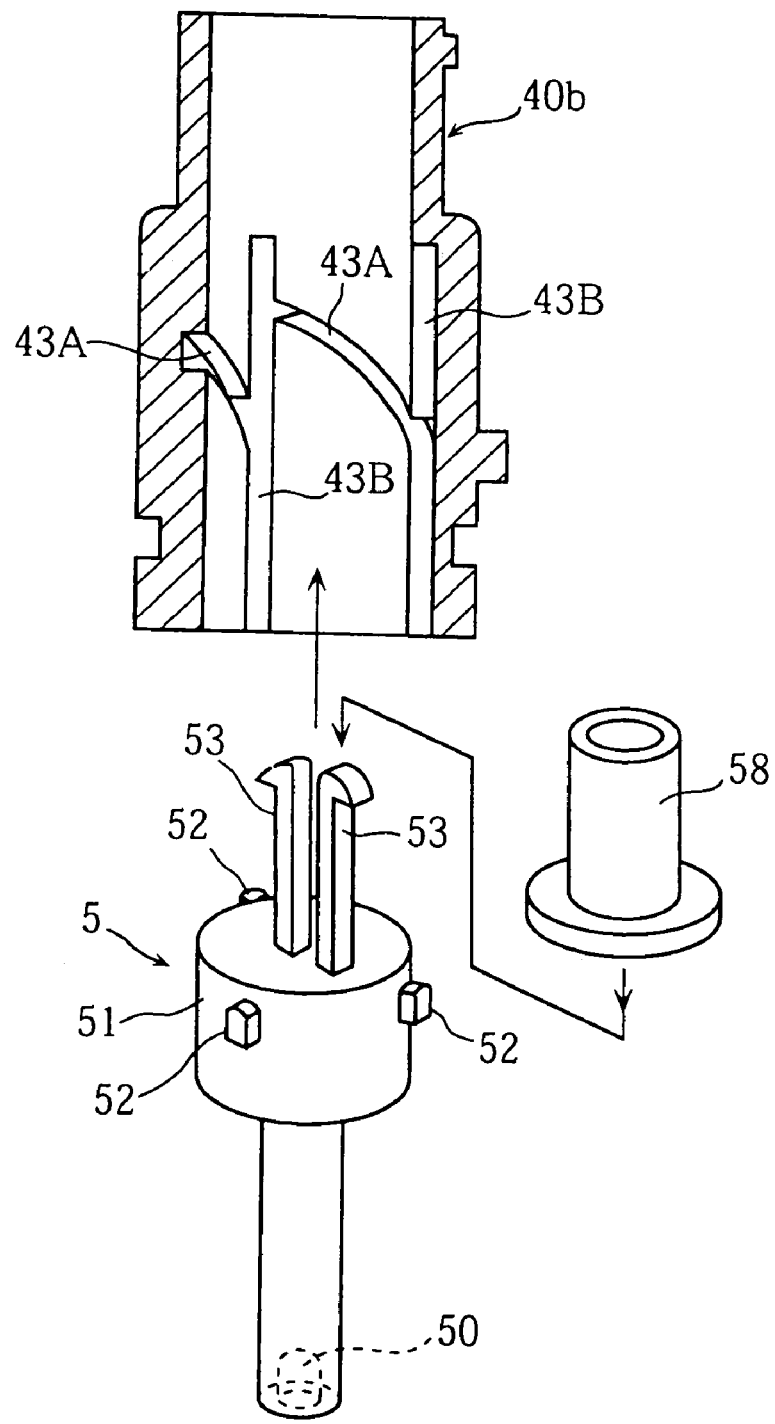
FIG. 9 illustrates the lancet holder and the sleeve for guiding the holder of the lancing apparatus shown in FIG. 7.

The inside of the recess 50 of the lancet holder 5 is formed with a plurality of grooves into which the ribs 22 of the body 20 can be fitted. With such an arrangement, when the body 20 of the lancet 2 is fitted into the recess 50, the relative rotation between the body 20 and the lancet holder 5 is prevented. As shown in FIG. 9, the lancet holder 5 has a head portion 51 having a circumferential surface formed with a plurality of equiangularly spaced projections 52. The projections 52 are fitted in and guided along a plurality of first guide grooves 43A and second guide grooves 43B formed at an inner wall surface of the sleeve 40b.

The first guide grooves 43A serve to rotate the lancet holder 5 when the lancet holder 5 is pushed upward by the lancet 2 of the lancing unit U. The first guide grooves are inclined relative to the axial direction of the sleeve 40b. The second guide grooves 43B serve to guide the straight movement of the lancet 2 and the lancet holder 5 when these parts are caused to advance toward the front end of the housing 4 to lance the skin of a human body with the lancet 2. The second guide grooves extend straight in the axial direction of the sleeve 40b. FIGS. 10A-10E are developed plan view of part of the first and the second guide grooves 43A and 43B, which are actually connected to each other. (In these figures, the nearby portions of the first and the second guide grooves 43A and 43B are hatched.) When the lancet holder 5 moves in the axial direction of the housing 4, the projections 52 move along the first and the second guide grooves 43A and 43B. The operation will be described later in detail.

As shown in FIGS. 7 and 8, the latch member 59 is connected to an upper portion of the lancet holder 5 and slidably accommodated in the housing 4. The latch member 59 has a lower end into which a bush 58 is non-rotatably fitted. In the bush 58, a plurality of projections 53 projecting from the upper surface of the lancet holder 5 are rotatably inserted. With such an arrangement, the lancet holder 5 is rotatable, whereas the latch member 59 does not rotate in accordance with the rotation of the lancet holder. The upper end of each of the projections 53 engages the upper end of the bush 58 so as not to drop therefrom, whereby the lancet holder 5 and the latch member 59 are connected to each other.

Figure 16:
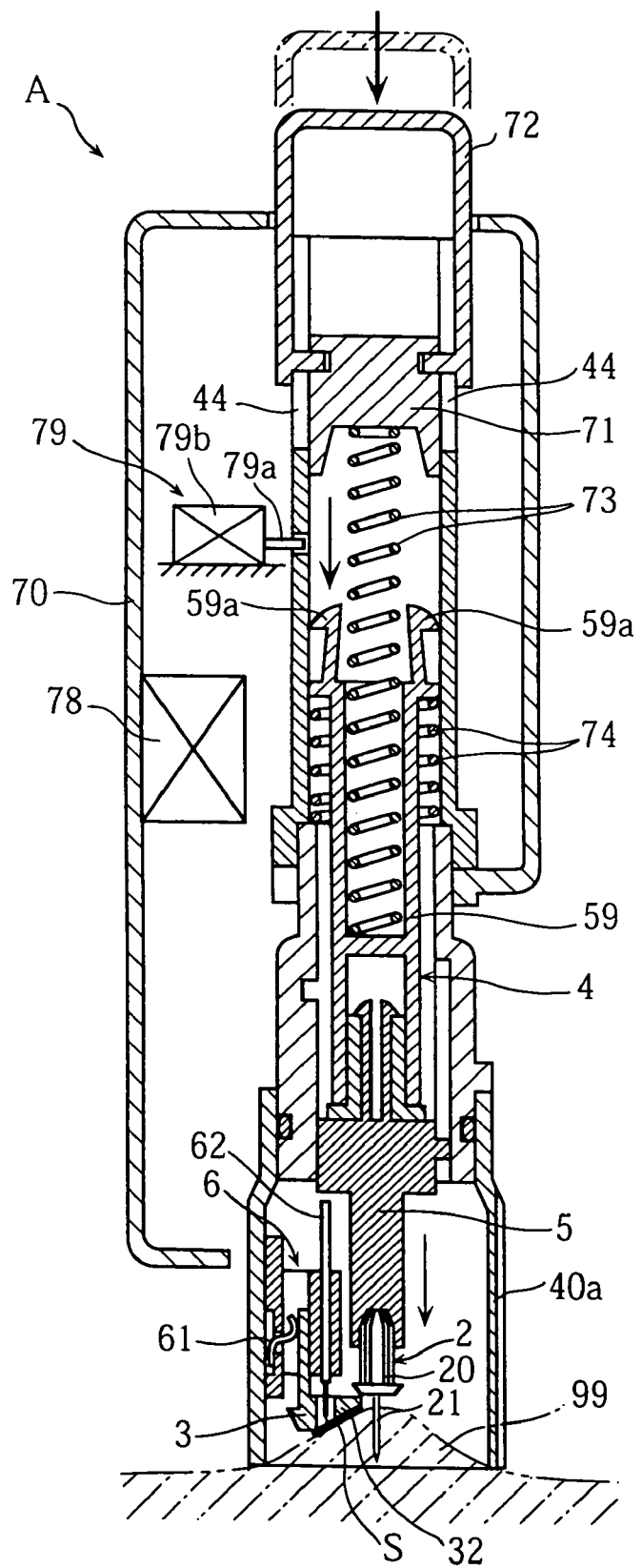
FIG. 16 is a sectional view showing an example of use of the lancing apparatus.

The latch member 59 has an upper portion formed with a pair of pawls 59a. Each of the pawls 59a serves to engage with an edge of a respective one of paired cutouts 44 formed in the sleeve 40c. As will be described later, this engagement occurs when the lancet holder 5 and the latch member 59 are pushed upward by the lancet 2 of the lancing unit U. To the upper portion of the sleeve 40c are mounted a pusher 71 for releasing the latch, and an operation cap 72 connected to the pusher. Between the pusher 71 and an intermediate wall 59b of the latch member 59 is provided a spring 73. The spring 73 may comprise a compression coil spring, for example. The operation cap 72 is slidable relative to the sleeve 40c in the axial direction thereof. Thus, when the operation cap 72 is pushed down while compressing the spring 73, the pusher 71 also moves downward in accordance with the movement of the operation cap to press the pawls 59a. As a result, as shown in FIG. 16, the pawls 59a are forcibly disengaged from the edges of the cutouts 44, whereby the latch member 59 and the lancet holder 5 advance downward due to the resilient force of the compressed spring 73. In the housing 4 is also provided a return spring 74 for retreating the lancet holder 5 and the latch member 59 after the advancement.

Referring to FIG. 7, the stopper mechanism 79 includes a stopper 79a in the form of a pin or a plate, and a driver 79b for moving the stopper 79a reciprocally in the direction indicated by the arrow N6, i.e., in the direction crossing the axial direction of the housing 4. The driver 79b may comprise a relatively small actuator utilizing electromagnetic force, for example. The stopper 79a is movable to advance its front end through a hole 49 provided in the circumferential wall of the housing 4 so that the front end enter the housing 4 and is located in the path of the reciprocal movement of the latch member 59. The stopper is also movable so that the front end comes toward the outer side of the housing 4 and retreats from the path of the reciprocal movement of the latch member. Specifically, when the latch member 59 and the lancet holder 5 are moved to advance downward as shown in FIG. 7, the stopper 79a is located in the reciprocal movement path at a position which is higher than the upper end of the latch member 59 and lower than the lower edges of the paired cutouts 44 of the housing 4. When the upper end of the latch member 59 comes into contact with the stopper 79a, further upward movement of the latch member 59 is prevented.

The usage and advantages of the lancing unit U and the lancing apparatus A will be described below.

In the lancing unit U, the first chamber 18A is hermetically closed by the film 14 before the use, as shown in FIGS. 1 and 2. Therefore, the reagent 39a of the sensor S is not exposed to e.g. moisture, whereby the quality deterioration in a short period of time is prevented. Since the needle 21 of the lancet 2 is covered by the cap 29 and the cap 29 is integrally formed on the body 20 of the lancet 2, the needle 21 is also hermetically sealed. Therefore, the sterilized state of the needle 21 can be properly maintained from the state before the lancet 2 is incorporated into the case 1.

The lancing unit U can be easily manufactured by mounting the lancet 2 provided with the cap 29 into the case 1, mounting the sensor holder 3 to the cap 29, and then sealing the opening 12A of the case 1 by the film 14. Specifically, the lancing unit U can be manufactured easily at a low cost particularly because the lancet 2 can be mounted just by fitting the hole 29a of the cap 29 to the projection 15 of the case 1 and the sensor holder 3 can be mounted just by fitting the paired holding walls 32b around the cap 29. In the lancing unit U, particular parts for supporting the lancet 2 and the sensor holder 3 within the case 1 need not be additionally provided. Therefore, the entire structure is relatively simple, which also contributes to a reduction in the manufacturing cost of the lancing unit U.

Figure 11:
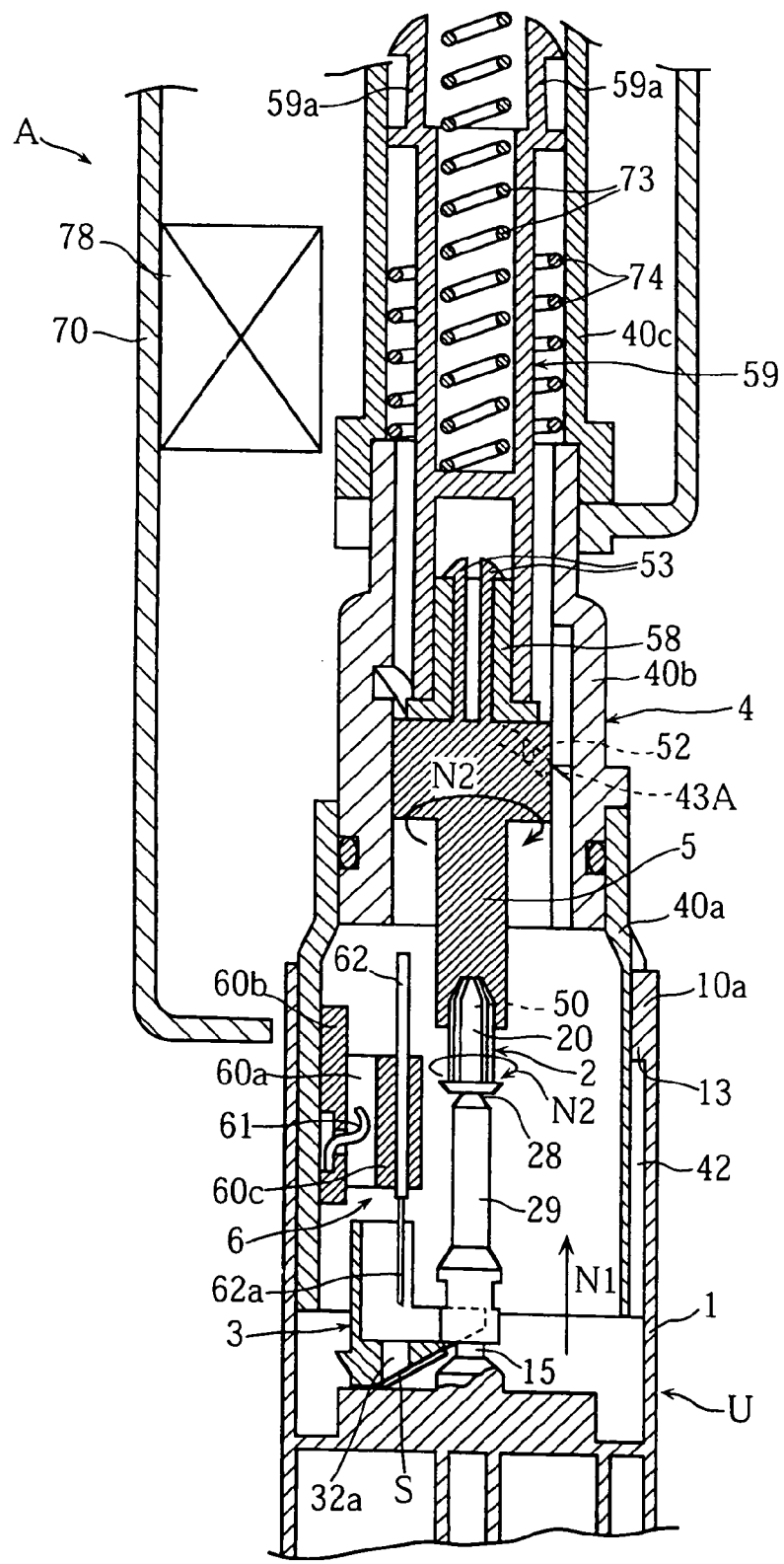
FIG. 11 is a sectional view of a principal portion in the process of mounting a lancet and a sensor holder to a lancing apparatus.

To use the lancing unit U, the film 14 is broken or peeled off to expose the opening 12A of the case 1, and then a portion of the case 1 which is closer to the first end 10a is fitted around the sleeve 40a of the lancing apparatus A, as shown in FIG. 11. By this operation, the body 20 of the lancet 2 is fitted into the recess 50 of the lancet holder 5 to be held by the lancet holder 5. In mounting the lancet 2 in this way, the stopper 79a is kept retreated from the housing 4. As the case 1 is slid upward in the direction indicated by the arrow N1, the lancet 2 pushes up the lancet holder 5 against the resilient force of the spring 73. As a result, the lancet holder 5 and the body 20 of the lancet 2 rotate in the direction indicated by the arrow N2, whereby the boundary portion 28 between the lancet 2 and the cap 29 is twisted and broken.

Figure 10A:
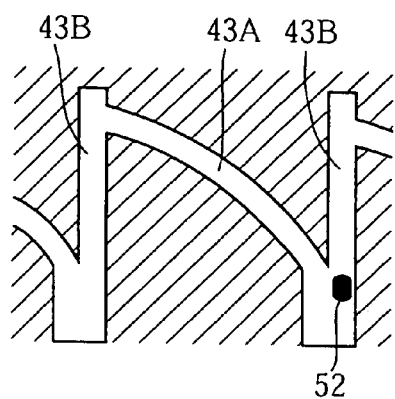
FIGS. 10A-10E illustrate the guiding of the projection of the lancet holder.
Figure 10B:
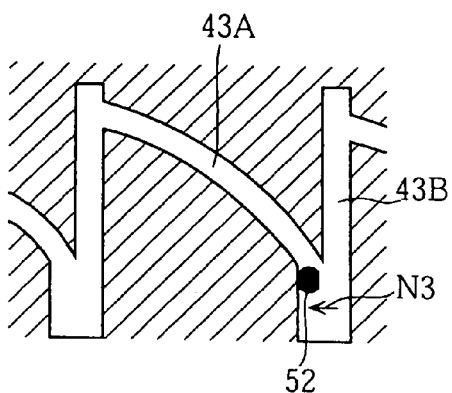

Specifically, as shown in FIG. 10A, the projection 52 of the lancet holder 5 is initially located within the second guide groove 43B. When the body 20 of the lancet 2 is fitted into the recess 50, the projection 52 moves closer to the first guide groove 43A, as indicated by the arrow N3 in FIG. 10B. To cause this movement, either the front ends of the ribs 22 of the body 20 or the grooves in the recess 50 are inclined to be helical so that the body 20 can exert a force to rotate the lancet holder 5 in the direction indicated by the arrow N3 when the body 20 is fitted into the recess 50.

Figure 10C:
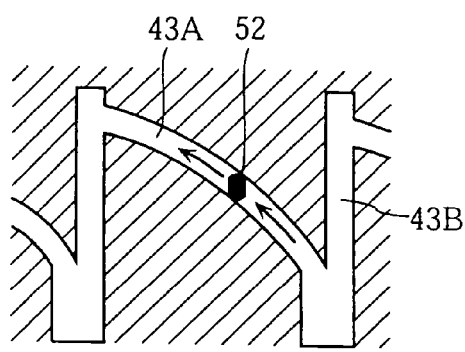
Figure 10D:
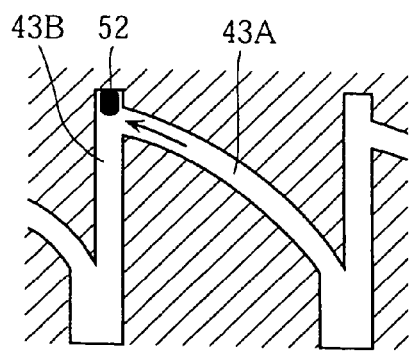

Subsequently, when the lancet holder 5 is pushed upward by the lancet 2, the projection 52 moves through the first guide groove 43A, as shown in FIGS. 10C and 10D. This operation causes the lancet holder 5 to rotate, whereby the body 20 of the lancet 2 also rotates. On the other hand, the cap 29 of the lancing unit U does not rotate because it is fixed to the case 1. Therefore, the boundary portion 28 between the body 20 of the lancet 2 and the cap 29 is twisted and broken.

As shown in FIG. 12, when the case 1 is pushed upward by an appropriate amount, the latch member 59 also moves upward, whereby each of the pawls 59*a* engages with an edge of a respective one of the cutouts 44. Thus, the latch member 59 is latched while compressing the spring 73. As shown in FIG. 13, when the case 1 is pushed upward, the side wall 31 of the sensor holder 3 enters the space 60*a* of the holding portion 6. In this embodiment, by sliding and fitting the case 1 relative to the sleeve 40*a* while preventing the rotation, each portion of the lancing unit U can be accurately positioned relative to a corresponding portion of the lancing apparatus A, whereby a high positioning accuracy can be provided. Therefore, even when the space 60*a* has a relatively small opening width, the sidewall 31 can be guided precisely into the space 60*a*. Moreover, the above-described fitting of the lancet 2 into the recess 50 of the lancet holder 5 can be performed precisely.

When the side wall 31 enters the space 60*a*, the side wall 31 receives the resilient force F of the spring 61. When the sensor holder 3 is supported by the cap 29, the sensor holder keeps its posture while resisting the resilient force F, whereby the gap 60*a'* is kept between the second wall 60*c* and the side wall 31. The front end 62*a* of each measurement probe 62 is pushed upward by the sensor S and brought in contact with the electrode 39*b* of the sensor S while exerting a resistive force to the pushing. In this way, each measurement probe 62 is reliably connected electrically to the relevant electrode 39*b*.

After the pushing up of the case 1 is completed in the above-described manner, the case 1 is pulled down for removal from the sleeve 40*a*, as shown in FIG. 14. Since the boundary portion 28 between the body 20 of the lancet 2 and the cap 29 has been twisted and broken as noted above, the lancet 2 and the cap 29 readily separate from each other. By this separation, the lancet 2 is duly mounted to the lancet holder 5 with the needle 21 exposed. When the case 1 is pulled down, the cap 29 slides relative to the sensor holder 3 and pulled out to locate below the sensor holder 3. Thus, the sensor holder 3 separated from the cap 29 is secured to the holding portion 6.

As noted above, in the lancing unit U and the lancing apparatus A, the mounting of the lancet 2 to the lancet holder 5, the separation of the cap 29 from the lancet 2, the mounting of the sensor holder 3 to the holding portion 6, the separation of the cap 29 from the sensor holder 3, and the latching of the latch member 59 can be performed just by sliding and fitting the case 1 around the sleeve 40*a* by an appropriate amount and then pulling out the case, which is convenient. The cap 29 is kept fixed to the case 1.

When the cap 29 is removed from the sensor holder 3, the side wall 31 of the sensor holder 3 is pressed against the second wall 60*c* by the resilient force F of the spring 61. Specifically, the sensor holder 3 moves toward the center of the sleeve 40*a* (in the direction indicated by the arrow N4 in FIG. 14) by the amount corresponding to the dimension of the gap 60*a'* shown in FIG. 13. In accordance with the movement of the sensor holder 3, the sensor S moves closer to the lancing position of the lancet 2, which provides the advantages which will be described later.

Figure 10E:
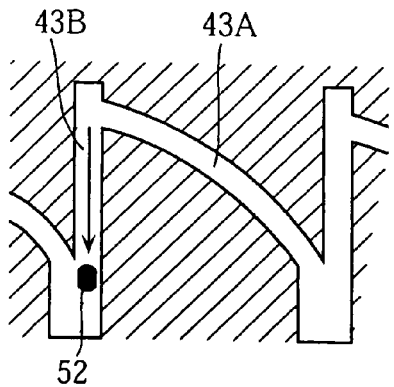
Figure 15:
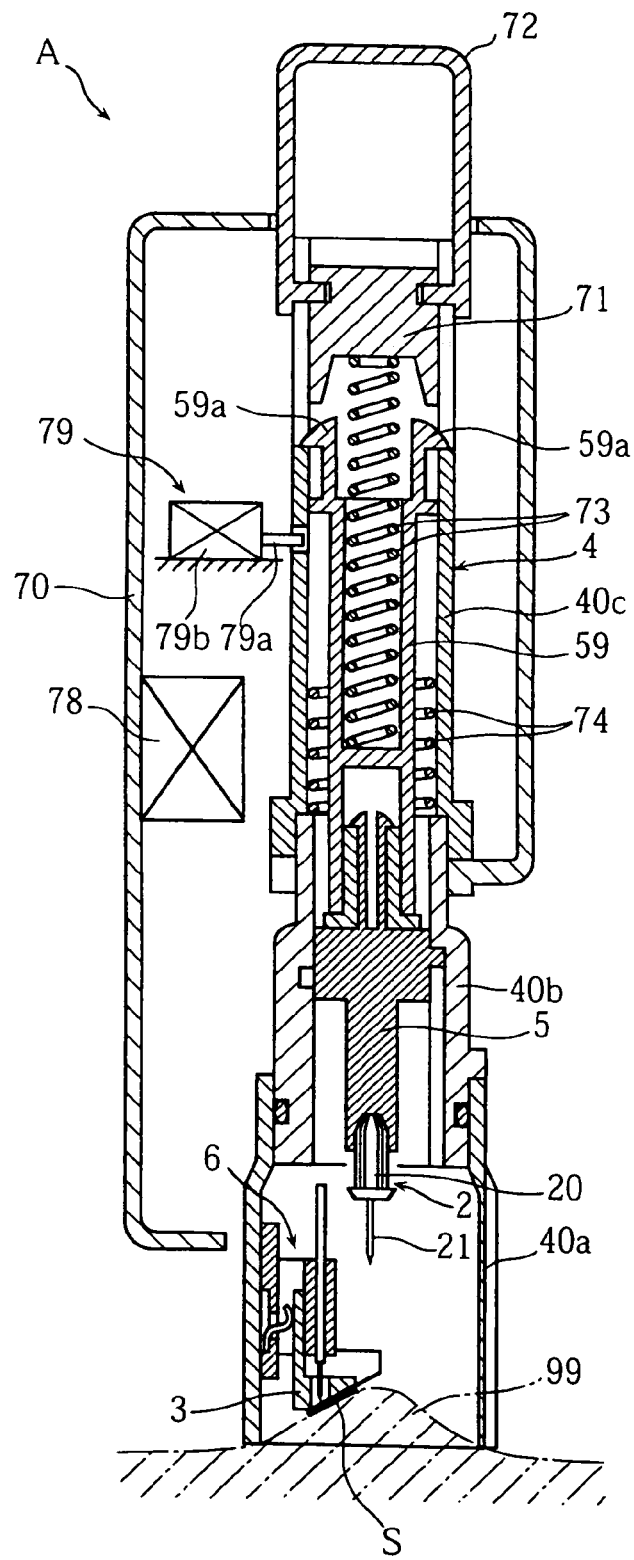
FIG. 15 is a sectional view showing an example of use of the lancing apparatus.

After the lancet 2 and the sensor holder 3 are mounted to the lancing apparatus A by the above-described manner, the lancing can be performed. To perform the lancing, the front end of the sleeve 40*a* of the lancing apparatus A is brought into contact with the skin 99 of a human body as the object to be lanced, as shown in FIG. 15. Subsequently, the operation cap 72 is pushed to advance the pusher 71. As a result, as shown in FIG. 16, each of the pawls 59*a* is disengaged from the edge of the relevant cutout 44, whereby the latch member 59 and the lancet holder 5 move downward by the resilient force of the spring 73 to cause the needle 21 of the lancet 2 to lance the skin 99. At this time, the body 20 of the lancet 2 partially engages the main wall 32 of the lancet holder 3, whereby the needle 21 is prevented from sticking deep into the skin 99 more than necessary. As shown in FIG. 10E, when the lancet holder 5 moves downward, the projection 52 moves along the second guide groove 43B, whereby the lancet holder 5 can move straight. As a result of the straight movement, the projection 52 can be located at a position which is similar to the initial position shown in FIG. 10A, which enables the repeating of the above operation.

After the needle 21 lances the skin 99, the latch member 59 and the lancet holder 5 immediately retreat by a predetermined amount due to the resilient force of the return spring 74 to pull out the needle 21 from the skin 99. Preferably, a pump or a pump mechanism is provided in the lancing apparatus A to generate a negative pressure in the sleeve 40*a* in lancing the skin. With such an arrangement, the negative pressure promotes the bleeding from the skin 99, so that the lancing amount of the needle 21 of the lancet 2 can be reduced, which is advantageous for reducing the damage to the skin 99.

The blood extracted from the skin 99 is applied to the sensor S and guided to the reagent 39*a* of the sensor S. Since the sensor holder 3 has approached the center of the sleeve 40*a*, i.e., located closer to the lancing position as described with reference to FIG. 14, the blood can be reliably applied to a predetermined portion of the sensor S.

As means for positioning the sensor holder 3 close to the center of the sleeve 40*a*, it may be considered to mount the sensor holder 3 close to the center of the case 1 from the first in the structure of the lancing unit U shown in FIGS. 1 and 2. However, since the sensor holder 3 is supported by the cap 29 in the lancing unit U, the wall thickness of the cap 29 need be reduced for positioning the sensor holder 3 close to the center of the case 1. When the wall thickness of the cap 29 is excessively reduced, the mechanical strength of the cap may be deteriorated. In such a case, the cap 29 may not reliably support the sensor holder 3. In this embodiment, however, such a problem can be reliably solved, because the sensor holder 3 moves closer to the center of the sleeve 40*a* when it is mounted to the lancing apparatus A.

After the lancing operation is performed, the control circuit 78 computes the glucose level in blood. In the lancing apparatus A, the computed value may be displayed at a display (not shown) comprising a liquid crystal display, for example.

Thereafter, the lancet 2 and the sensor holder 3 after use are removed from the lancing apparatus A. In the removing operation, the orientation of the case 1 is reversed from that in mounting the lancet 2, and a portion of the case 1 which is closer to the second end 10*b* is fitted around the sleeve 40*a*. As a result, the first and the second engagement projections 19A and 19B enter the sleeve 40*a*. When the front ends of the first and the second engagement projections 19A and 19B come into contact with the downward surfaces 24*b* and 34*b* of the engagement steps 24 and 34, the engagement projections 19A and 19B resiliently flex and easily pass over the surfaces 24*b* and 34*b*. Therefore, as shown in FIG. 18, the pawls 19*a* and 19*b* can reach beyond the engagement steps 24 and 34 for engagement with the engagement steps 24 and 34. Since the surfaces 24*b* and 34*b* are inclined, the above engagement operation can be performed smoothly. To perform the engagement operation more smoothly, it is preferable that the upper surfaces of the first and the second engagement projections 19*a* and 19B are inclined as illustrated.

Figure 17:
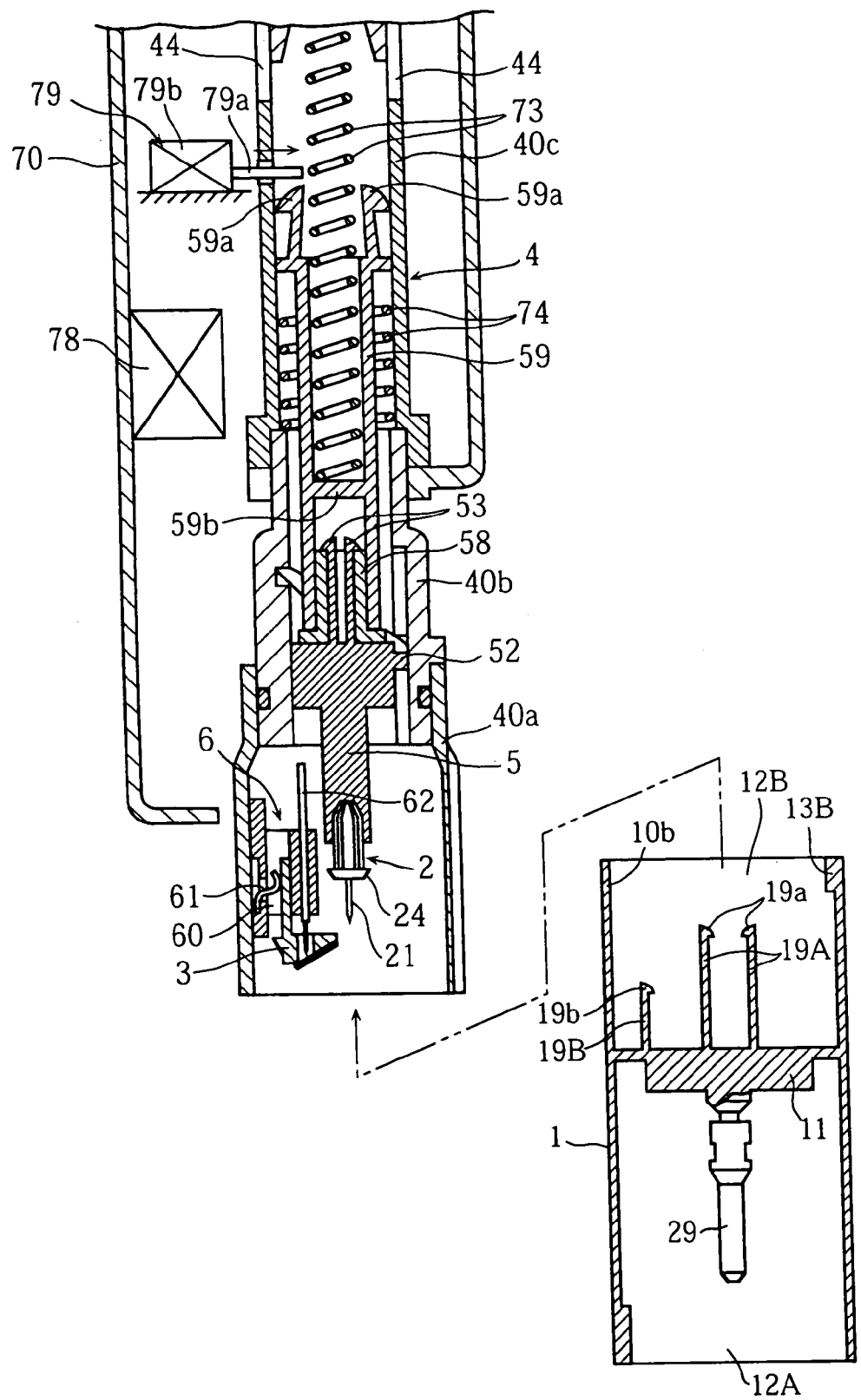
FIG. 17 is a sectional view of a principal portion showing the operation of removing the lancet and the sensor holder from the lancing apparatus.

In the above engagement, the lancet holder 5 temporarily receives the upward pressing force from the first engagement projections 19A. To cope with this, as shown in FIG. 17, the stopper 79a is caused to project into the housing 4 before the engagement is performed. With such an arrangement, it is possible to prevent the upward movement of the latch member 59 and the resulting unnecessary latching of the latch member 59. By the prevention of the upward movement of the latch member 59, the lancet holder 5 can be kept at a constant height when the first engagement projections 19A are moved upward. Therefore, the engagement of the first engagement projections 19A with the engagement step 24 can be performed reliably.

Figure 19:
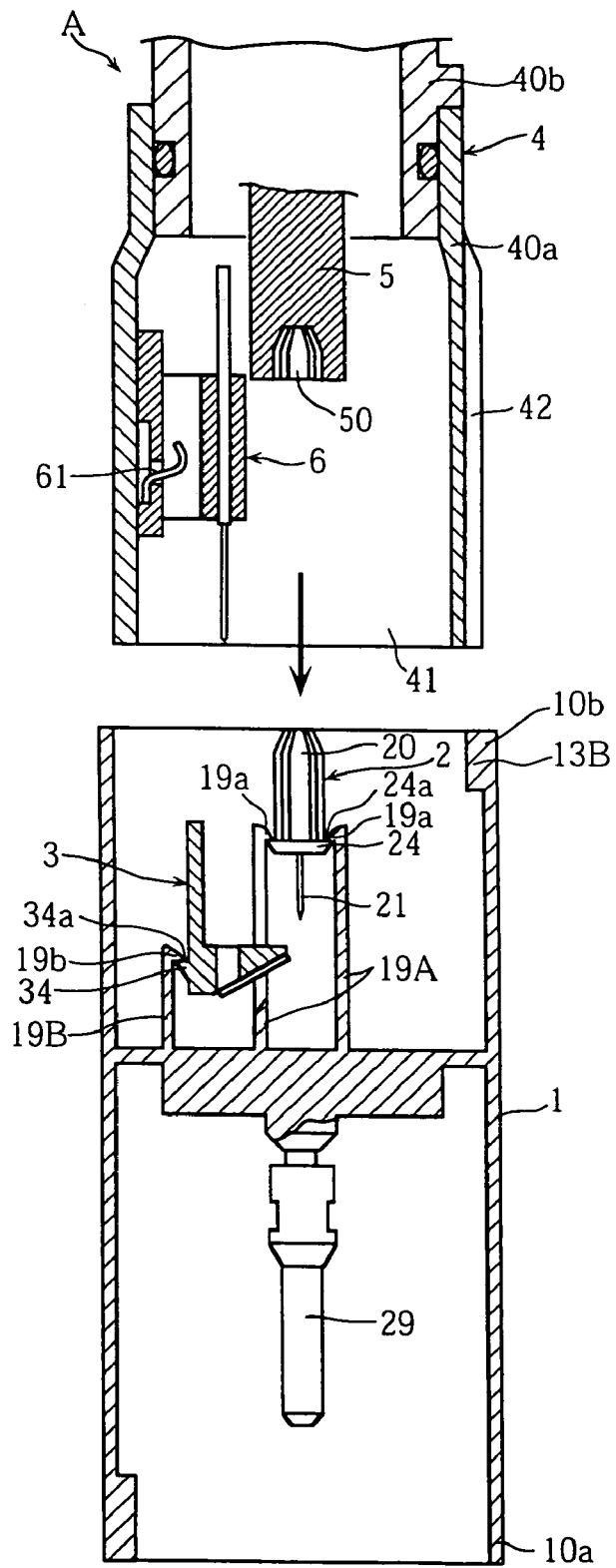
FIG. 19 is a sectional view showing a principal portion after the removal of the lancet and the sensor holder from the lancing apparatus is completed.

Subsequently, as shown in FIG. 19, the case 1 is pulled downward for removal from the housing 4. Since the first and the second engagement projections 19A, 19B are held in engagement with the lancet 2 and the sensor holder 3, the lancet 2 and the sensor holder 3 can be removed from the lancet holder 5 and the holding portion 6 by moving the case 1 downward.

The lancing unit U of this embodiment have the following advantages.

In pulling the lancet 2 out of the lancet holder 5, a downward pulling force is exerted, while the pawls 19a of the first engagement projections 19a engage the upward surface 24a of the engagement steps 24. Therefore, the engagement between the pawls 19a and the upward surface 24a is reliably maintained. Therefore, unlike the prior art structure, the first engagement projections 19A can reliably hold the lancet 2, whereby the lancet 2 can be removed reliably. The arrangement of the paired engagement projections 19A to hold the lancet 2 from opposite sides further ensures the engagement.

Since the first engagement projections 19A engage the lancet 2 reliably as noted above, a strong pulling force can be exerted to the lancet 2 in pulling the lancet 2 out of the lancet holder 5. Therefore, even when the lancet holder 5 holds the lancet 2 with a strong holding force, the lancet 2 can be removed properly. Therefore, as the means for holding the lancet 2 by the lancet holder 5 while preventing easy dropping of the lancet, the means for closely fitting the lancet 2 into the recess 50 of the lancet holder 5 may be employed. Unlike the prior art structure, threading of the lancet 2 and the lancet holder 5 for screwing these parts together is not necessary in this embodiment, whereby the structure can be simplified.

Although only a single second engagement projection 19B is used for the sensor holder 3, the engagement between the pawl 19b of the second engagement projection 19B and the upward surface 34a of the engagement step 34 can be reliably performed similarly to the engagement between the first engagement projections 19A and the lancet 2. Therefore, the removal of the sensor holder 3 from the holding portion 6 can be performed properly.

Similarly to the mounting of the lancet 2 and the sensor holder 3, the removal of the lancet 2 and the sensor holder 3 described above can be performed by one-touch operation, i.e., just by fitting and removing the case 1 relative to the front end of the housing 4. Therefore, the operation is easy. Since the lancet 2 and the sensor holder 3 after use are accommodated in the case 1, the user need not touch the lancet 2 and the sensor holder 3. Therefore, the disposal of these parts can be performed hygienically. Since the cap 29 is also accommodated in the case 1, these parts can be collectively disposed of easily. The lancing unit U of this embodiment can be used for mounting the lancet 2 and the sensor holder 3 to the lancing apparatus A as well as for removing the lancet 2 and the sensor holder 3 from the lancing apparatus A, which is convenient.

FIGS. 20-25 show other embodiments of the present invention. In these figures, the elements which are identical or similar to those of the foregoing embodiment are designated by the same reference signs as those used for the foregoing embodiment.

Figure 20A:
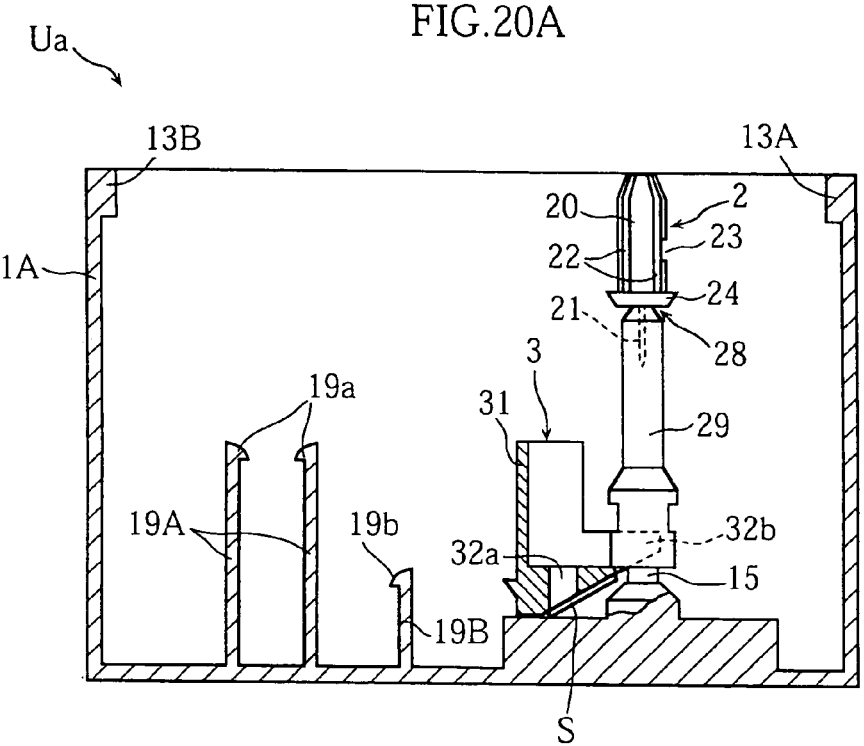
Figure 20B:
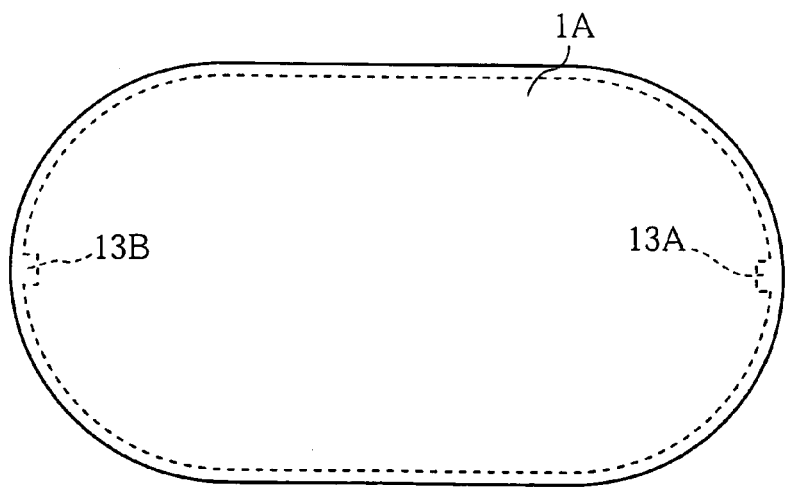
FIG. 20B is its bottom view.

The lancing unit Ua shown in FIG. 20A includes a case 1A having an open end. The inside of the case 1A is not partitioned. In the case 1A are provided a lancet 2, a cap 29, a sensor holder 3, a pair of first engagement projections 19A and a second engagement projection 19B. As shown in FIG. 20B, the case 1A has a generally oval cross section having a first and a second longitudinally-opposite end edges. The lancet 2, the cap 29 and the sensor holder 3 are arranged at a position offset from the center of the case 1A toward the first end edge. The first and the second engagement projections 19A and 19B are arranged at a position offset from the center of the case 1A toward the second end edge. The end edges of the case 1 have arcuate inner surfaces formed with projections 13A and 13B, respectively.

With the above arrangement, the lancet 2 and the sensor holder 3 can be mounted to the lancing apparatus A by fitting a portion of the case 1 which is closer to the first end edge to the sleeve 40a of the lancing apparatus A shown in FIG. 7 and then pulling out the case from the sleeve. The lancet 2 and the sensor holder 3 can be removed from the lancing apparatus by fitting a portion of the case 1 which is closer to the second end edge to the sleeve 40a of the lancing apparatus A and then pulling out the case from the sleeve. In fitting the case 1A to the sleeve 40a, the rotation of the case 1A can be prevented by fitting the projection 13A or 13B into the groove 42 formed at the sleeve 40a. Therefore, each portion in the case 1A can be precisely guided to the relevant portion of the lancing apparatus. In the present invention, like the lancing unit Ua of this embodiment, predetermined parts or portions may be arranged in a single chamber of a case. With such an arrangement, in removing the lancet from the lancing apparatus, it is not necessary to reverse the case.

Figure 21:
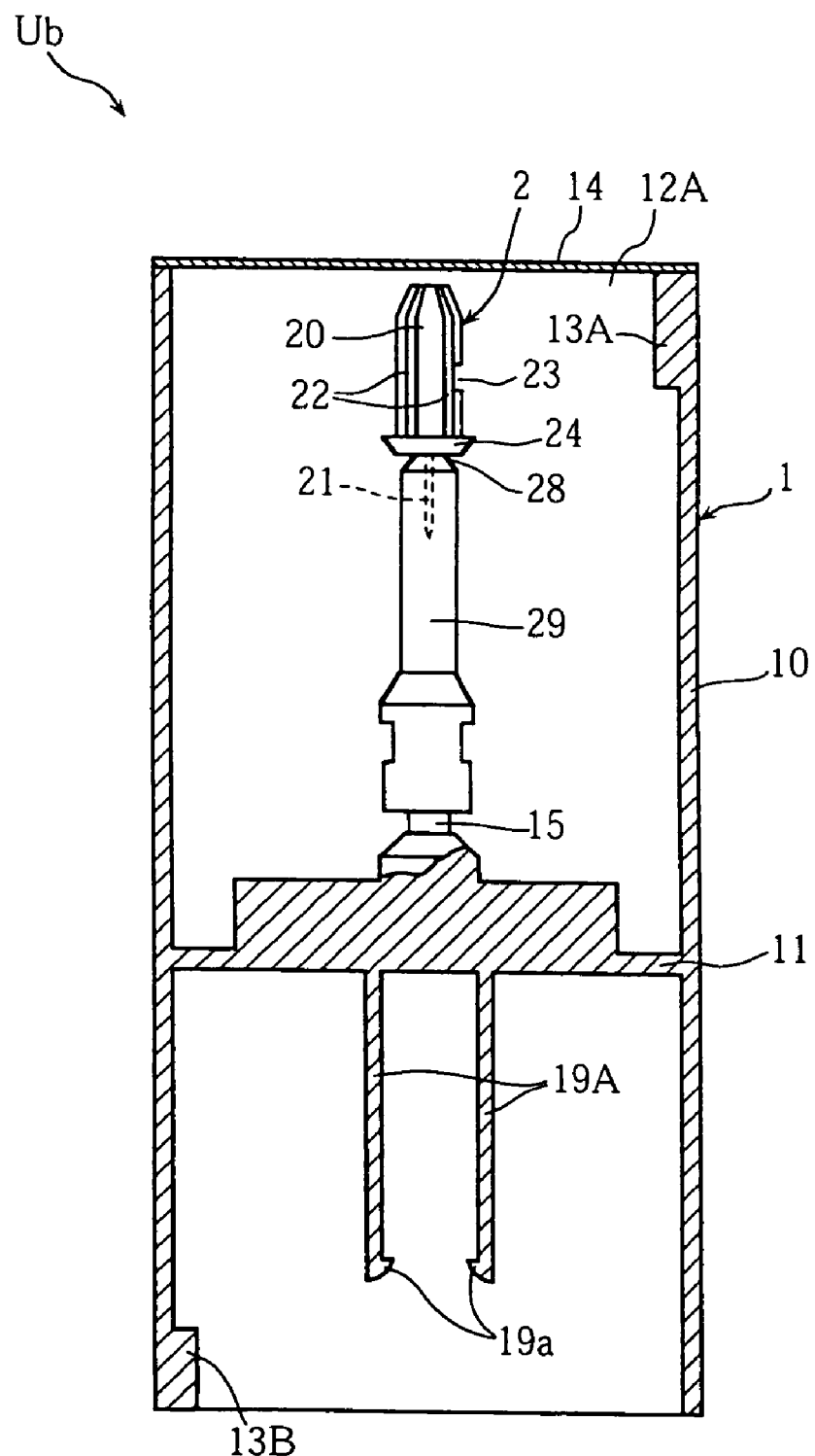
FIG. 21 is a sectional view showing another example of lancing unit according to the present invention.

The lancing unit Ub shown in FIG. 21 does not include parts or portions corresponding to the sensor holder 3 and the second engagement projection 19B of the foregoing embodiments. In the case 1 are provided a lancet 2, a cap 29 and a pair of first engagement projections 19A. Some lancing apparatuses have a simple structure just for causing bleeding by lancing the skin of e.g. a human body with a needle of a lancing member. For the adaptation to such a lancing apparatus, like the lancing unit Ub of this embodiment, the lancing unit of the present invention may not include an analytical part such as a sensor holder 3 and the function for attaching or removing such an analytical part.

Figure 22A:
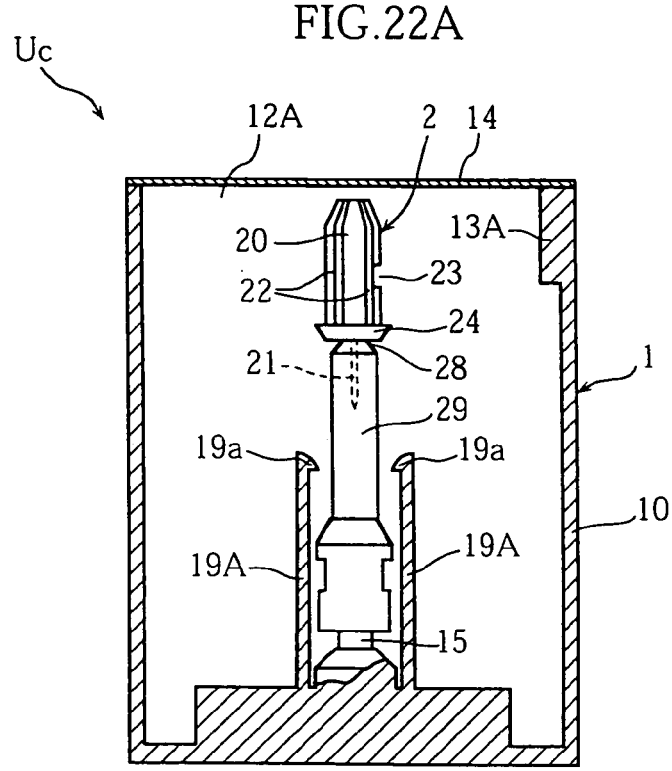
Figure 22B:
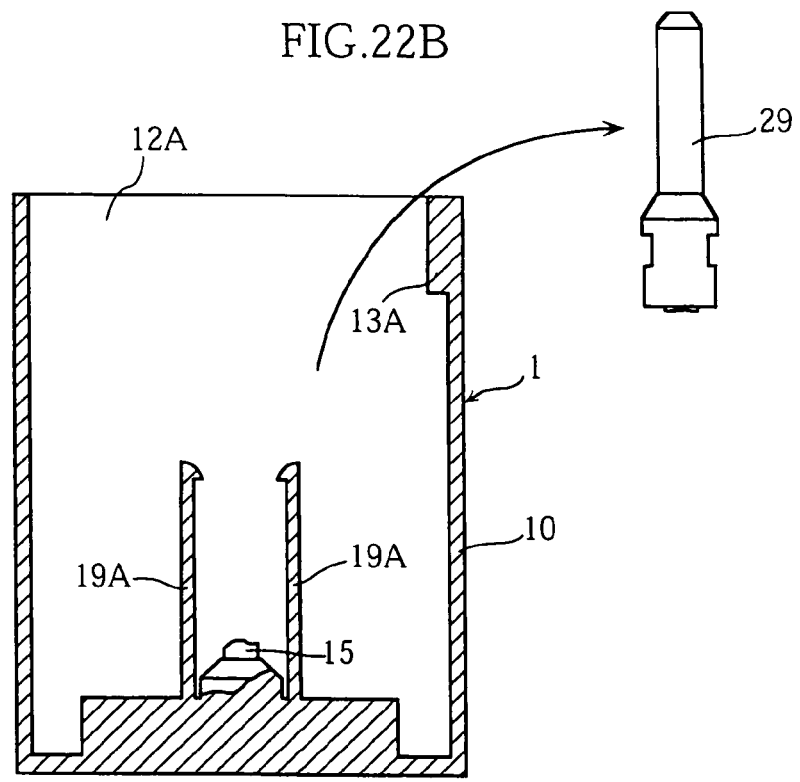
FIG. 22B is a sectional view showing the state in use.

In the lancing unit Uc shown in FIG. 22A, a pair of first engagement projections 19A are provided adjacent the cap 29 to flank the cap 29. In removing the lancet 2 mounted to a lancing apparatus, the cap 29 is removed from the case 1 by breaking the projection 15, for example, as shown in FIG. 22B. As a result, the cap 29 does not exist near the first engagement projections 19A. Therefore, by using the first engagement projections 19A, the lancet 2 can be properly removed from the lancing apparatus. In the lancing unit Uc, the first engagement projections 19A can be arranged close to the cap 29 and the lancet 2. Accordingly, the case can be made smaller than those of the lancing unit U, Ua and Ub described above.

Figure 23A:
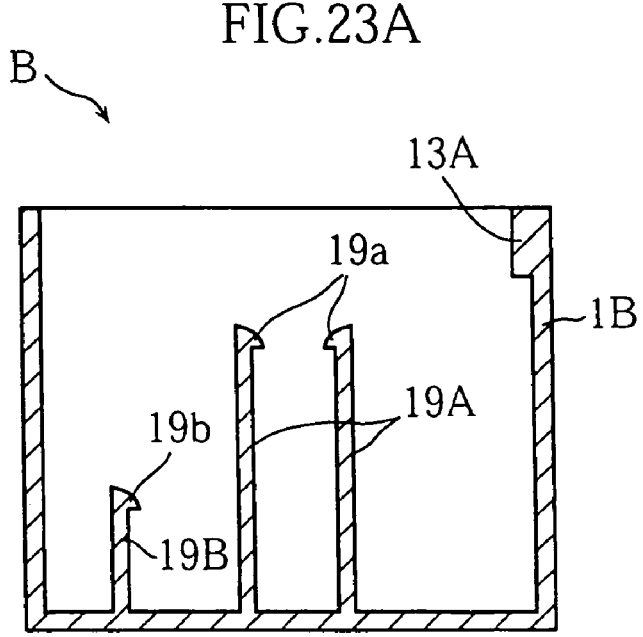
Figure 23B:
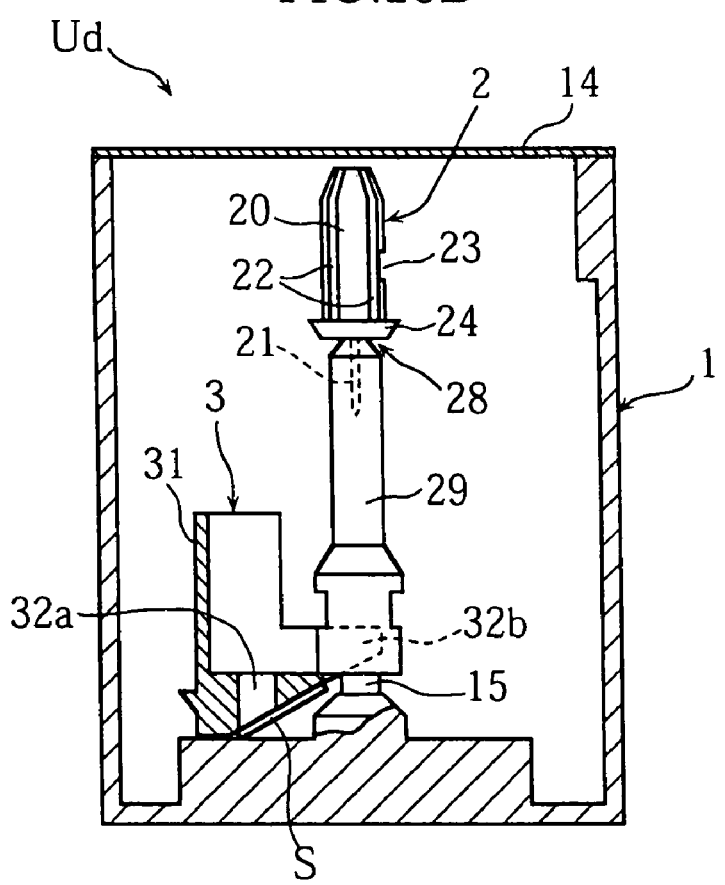
FIG. 23B is a sectional view showing an example of lancing unit to which the removal tool is applicable.

FIG. 23A shows a lancing member removal tool B. The tool includes a case 1B formed with a projection 13A, and a pair of first engagement projections 19A and a second engagement projection 19B provided in the case 1B. The case 1B does not incorporate members corresponding to a lancet 2 and a sensor holder 3. The removal tool B having such a structure is prepared separately from such a lancing unit Ud as shown in FIG. 23B and utilized for removing the lancet 2 and the sensor holder 3 mounted to a lancing apparatus by using the lancing unit Ud. The removal using the removal tool provides the same advantages as those described as to the lancing unit U shown in FIGS. 1 and 2. In this way, the present invention can be adapted for a removal tool just for removing predetermined members from a lancing apparatus. The removal tool may not include a second engagement projection and serve as a tool for removing the lancing member alone.

Figure 24A:
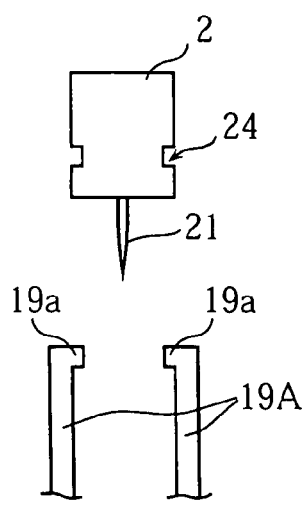
FIGS. 24A-24C show other examples of engagement step provided in a lancing member and engagement projection for engagement with the engagement steps.
Figure 24B:
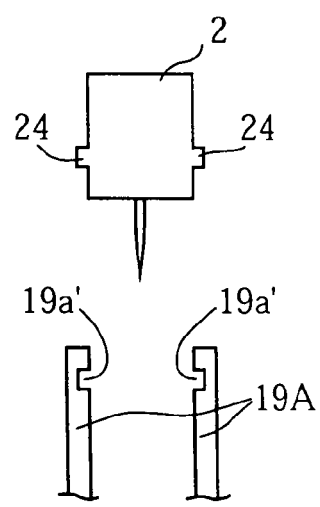
Figure 24C:
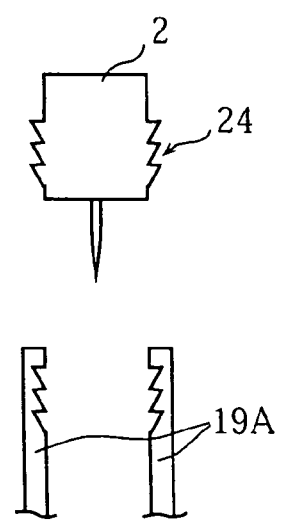

FIGS. 24A-24C show other examples of engagement step 24 to be provided at the lancet 2 and paired first engagement projections 19A for engagement with the engagement steps. In the example shown in FIG. 24A, the engagement step 24 is provided by a retreated portion, whereas the pawl 19*a* of each first engagement projection 19A has a shape for fitting into the retreated portion 24. In the example shown in FIG. 24B, the engagement step 24 of the lancet 2 is provided by a protrusion, whereas each first engagement projection 19A has a front end formed with a retreated portion 19*a'* having a shape for fitting to the protrusion. In the example shown in FIG. 24C, the engagement step 24 of the lancet 2 is provided by a plurality of male portions and female portions, whereas each first engagement projection 19A has a front end correspondingly formed with a plurality of female portions and male portions.

In this way, in the present invention, the configuration and number of engagement steps provided at the lancing member and the configuration of the engagement projections for engaging the engagement steps can be varied appropriately. The engagement means of the present invention may have any configuration as long as it is engageable with a surface of the lancing member in entering the housing of the lancing apparatus through the opening, the surface being oriented toward the rear side of the housing. In the case where the engagement means is provided by engagement projections, a pair of engagement projections need not necessarily be provided, and more than two projections or only a single projection may be provided.

Figure 25:
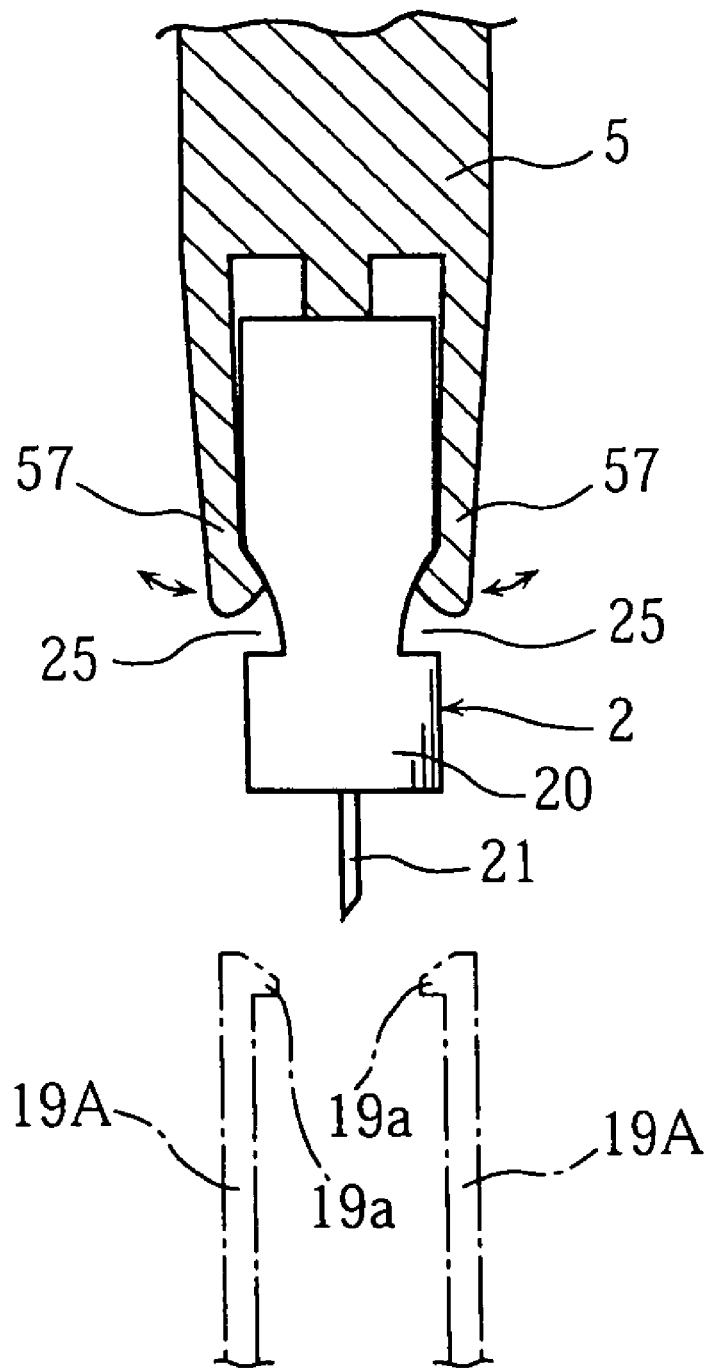
FIG. 25 is a sectional view showing another example of structure for fitting and mounting the lancing member.
Figure 26A:
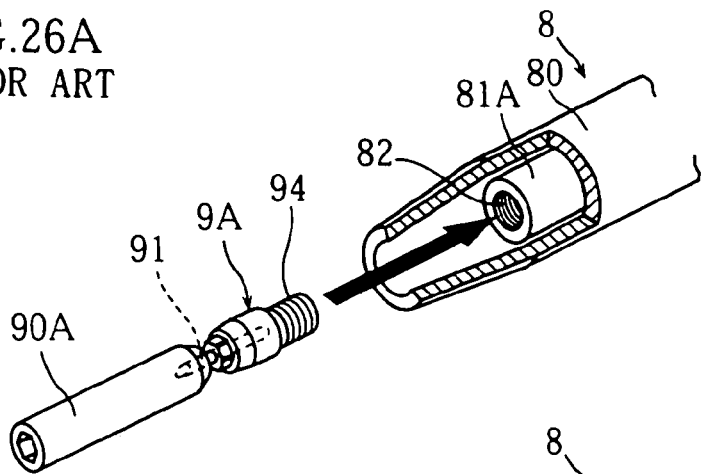
FIGS. 26A and 26B show an example of prior art structure.
Figure 26B:
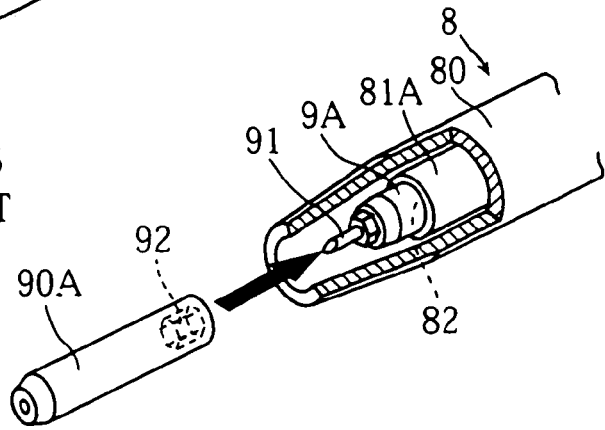
Figure 27A:
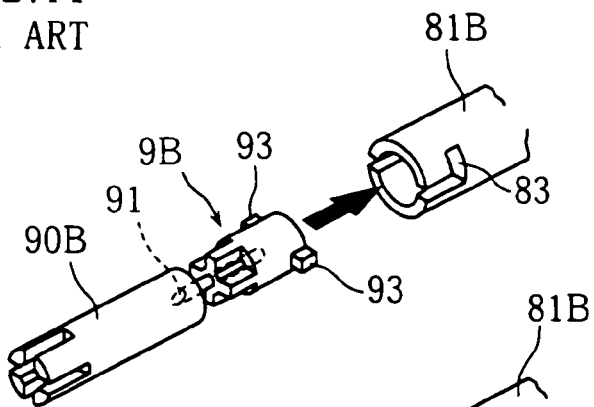
FIGS. 27A and 27B show another example of prior art structure.
Figure 27B:
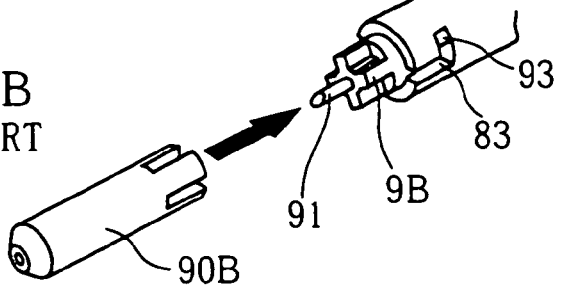

FIG. 25 shows a lancet holder 5 which includes a plurality of engagement projections 57 for holding a lancet 2 inwardly of the projections 57. The outer circumferential surface of the body 20 is formed with a recess 25 for engaging the front end of each engagement projections 57. This engagement prevents the lancet 2 from dropping unintentionally from the front end of the lancet holder 5. Such an engagement structure may be employed in the present invention for holding the lancet in a lancet holder. Although the present invention requires that the lancing member is capable of being fitted to the movable member, the above structure in which the lancet is partially received in a plurality of engagement projections is also included in the "fitting" of the present invention. To remove the lancet 2 held as shown in FIG. 25, the pawls 19*a* at the front ends of the engagement projections 19A may be brought into engagement with the recess 25 of the lancet 2, for example.

The present invention is not limited to the foregoing embodiments. Specific structure of each part of the lancing unit, the lancing member removal tool and the lancing apparatus according to the present invention may be modified in various ways.

The support member of the lancing unit according to the present invention may not include a cap for covering the needle of the lancing member or may not be in the form of a case having an open end or opposite open ends. As the lancing member, use may be made of one having a structure which is different from that of the lancet of the foregoing embodiments.

The lancing apparatus and the lancing unit of the present invention are not limited to those used for measuring the glucose level in blood but may be used for other kinds of measurement and analysis. The analytical part of the present invention is not limited to a sensor holder to which a sensor with a reagent is mounted but may comprise any member as long as it is at least capable of taking a sample obtained by lancing. For example, the analytical part may simply comprise a sensor including a substrate provided with a reagent, a test piece, or a small piece just for taking a sample.

In the lancing apparatus of the present invention, the driver only for operating the stopper may be dispensed with. For example, the stopper may be structured to be manually operated by the user so that the user can shift the position of the stopper. In the present invention, the stopper may be brought into direct engagement with the movable member (lancet holder) to which the lancet is mounted to prevent the retreating movement.

The invention claimed is:

1. A lancet unit for supplying a lancet to and removing the lancet from a lancing apparatus which includes a housing having a front end formed with an opening and a movable member provided in the housing reciprocally movably, the housing and the movable member being positioned outside of the lancet unit prior to attachment of the lancing apparatus to the lancet unit the lancet unit being attachable to the front end of the lancing apparatus and comprising:

a case provided separately from and configured to be temporarily attached to the housing of the lancing apparatus at the time of supplying the lancet to and removing the lancet from the lancing apparatus;

a support member provided in the case for removably supporting the lancet within the case; and engagement means provided adjacent to the support member within the case for removing the lancet from the lancing apparatus;

wherein the lancet is supplied from the support member to the movable member when the case is attached to the housing in a first state, the lancet including an engagement surface which is oriented toward a rear side of the housing when the lancet is mounted to the movable member; and wherein the engagement means is configured to be inserted into the housing of the lancing apparatus through the opening for engagement with the engagement surface of the lancet for subsequent removal of the lancet from the movable member of the lancing apparatus when the case is attached to the housing of the lancing apparatus in a second state.

2. The lancet unit according to claim 1, wherein the lancet includes a needle, and a body supporting the needle.

3. The lancet unit according to claim 2, wherein the body has an outer circumferential surface formed with a stepped portion comprising a recess or a projection, the engagement surface being provided by the stepped portion.

4. The lancet unit according to claim 3, wherein the engagement means includes at least one engagement projection extending in a first direction in which the needle of the lancet extends and having a front end formed with a pawl projecting in a second direction crossing the first direction.

5. The lancet unit according to claim 4, wherein the engagement means includes a plurality of engagement projections, and wherein the engagement projections are engageable with the engagement surface in such a manner as to clip the lancet when the case is attached to the housing of the lancing apparatus in the second state.

6. The lancet unit according to claim 5, wherein the stepped portion of the body comprises a flange;
wherein pawls of the engagement projections are spaced from each other by a distance which is smaller than an outer diameter or a width of the stepped portion; and
wherein, when the engagement projections are inserted into the housing in the second state, each of the engagement projections resiliently deforms in the second direction due to contact with the stepped portion so that each of the pawls passes over the stepped portion.

7. The lancet unit according to claim 2, wherein the support member includes a cap for covering the needle of the lancet and removably supporting the lancet.

8. The lancet unit according to claim 7, wherein a boundary portion between the body and the cap has a structure which is more liable to receive stress than other portions of the body and the cap.

9. The lancet unit according to claim 7, wherein the case includes a partition wall partitioning an interior of the case into a first and a second chambers adjoining each other in an axial direction of the housing; and
wherein the cap, the lancet and the analytical parts are arranged in the first chamber, whereas the engagement means is arranged in the second chamber.

10. The lancet unit according to claim 9, further comprising a lid for hermetically closing the first chamber.

11. The lancet unit according to claim 7, wherein the case includes a chamber for accommodating the cap, the lancet and the analytical part, and wherein the engagement means is also arranged in the chamber.

12. The lancet unit according to claim 2, further comprising an analytical part provided separately from the lancet and additional engagement means both provided in the case;
wherein the analytical part is removably supported by the support member so that the analytical part can be mounted at a predetermined position in the lancing apparatus in supplying the lancet to the movable member when the case is attached to the housing of the lancing apparatus in the first state, the analytical part including an additional engagement surface which is configured to be oriented toward the rear side of the housing when the analytical part is mounted to the predetermined position; and
wherein, when the additional engagement means is inserted through the opening into the housing in the first state in which the analytical part is separated from the support member and mounted to the predetermined position in the lancing apparatus, the additional engagement means engages the additional engagement surface of the analytical part.

13. The lancet unit according to claim 12, wherein the additional engagement means includes an additional engagement projection extending in a first direction in which the needle of the lancet extends and having a front end formed with a pawl projecting in a second direction crossing the first direction.

14. A lancet removal tool for removing a lancet from a movable member of a lancing apparatus, the lancing apparatus including a housing which has a front end formed with an opening and in which the movable member is arranged reciprocally movably, the housing and the movable member being positioned outside of the lancet removal tool prior to attachment of the lancing apparatus to the lancet removal tool the lancet having an engagement surface oriented toward a rear side of the housing,
the removal tool being attachable to the front end of the lancing apparatus and comprising:
a case provided separately from and configured to be temporarily attached to the housing of the lancing apparatus at the time of removing the lancet from the lancing apparatus;
a support member provided in the case, the support member being configured to removably support the lancet; and
engagement means provided adjacent to the support member within the case and configured for entering the housing through the opening for engagement with the engagement surface of the lancet when the case is attached to the housing of the lancing apparatus, the engagement means pulling the lancet from the movable member out of the housing when the case is detached from the housing.

15. The lancing member removal tool according to claim 14, further comprising additional engagement means provided in the case;
wherein, when the case is slid along and fitted to the front end of the housing with an analytical part mounted to a predetermined position in the lancing apparatus, the additional engagement means enters the housing through the opening and engages an additional engagement surface of the analytical part, the additional engagement surface being oriented toward the rear side of the housing.

* * * * *